United States Patent
Haetzelt et al.

(10) Patent No.: US 11,014,938 B2
(45) Date of Patent: *May 25, 2021

(54) COMPOSITIONS COMPRISING PRECURSORS FOR VOLATILES

(71) Applicant: Henkel AG & Co. KGaA, Duesseldorf (DE)

(72) Inventors: Andre Haetzelt, Eimeldingen (DE); Andreas Bauer, Kaarst (DE); Marc Weyhe, Krefeld (DE); Ursula Huchel, Cologne (DE); Thomas Gerke, Duesseldorf (DE); Christian Kropf, Hilden (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/652,687

(22) PCT Filed: Sep. 25, 2018

(86) PCT No.: PCT/EP2018/075921
§ 371 (c)(1),
(2) Date: Apr. 1, 2020

(87) PCT Pub. No.: WO2019/068509
PCT Pub. Date: Apr. 11, 2019

(65) Prior Publication Data
US 2020/0317688 A1  Oct. 8, 2020

(30) Foreign Application Priority Data

Oct. 4, 2017 (DE) .................... 10 2017 122 977.9

(51) Int. Cl.
| | | |
|---|---|---|
| C07D 498/04 | (2006.01) | |
| A61K 8/49 | (2006.01) | |
| A61Q 13/00 | (2006.01) | |
| A61Q 15/00 | (2006.01) | |
| C07D 263/06 | (2006.01) | |
| C11D 3/50 | (2006.01) | |

(52) U.S. Cl.
CPC .............. *C07D 498/04* (2013.01); *A61K 8/49* (2013.01); *A61Q 13/00* (2013.01); *A61Q 15/00* (2013.01); *C07D 263/06* (2013.01); *C11D 3/507* (2013.01)

(58) Field of Classification Search
None
See application file for complete search history.

(56) References Cited

U.S. PATENT DOCUMENTS

| | | |
|---|---|---|
| 2008/0305063 A1 | 12/2008 | Huchel et al. |
| 2009/0312231 A1 | 12/2009 | Huchel et al. |
| 2020/0317687 A1* | 10/2020 | Haetzelt .................. A61K 8/49 |

FOREIGN PATENT DOCUMENTS

| | | |
|---|---|---|
| EP | 2144917 B1 | 9/2012 |
| WO | 2007087977 A1 | 8/2007 |

OTHER PUBLICATIONS

Indradas et al., "Autoxidation as a trigger for the slow release of volatile perfumery chemicals", Flavour and Fragrance Journal, 2014, pp. 313-323, vol. 29, John Wiley & Sons, Ltd.

Trachsel et al., "Preparation of Imidazolidin-4-ones and Their Evaluation as Hydrolytically Cleavable Precursors for the Slow Release of Bioactive Volatile Carbonyl Derivatives", European Journal of Organic Chemistry, 2012, pp. 2837-2854, Wiley-VCH Verlag GmbH & Co. KGaA, Weinheim.

International search report from parallel PCT Patent Application PCT/EP2018/075921 dated Nov. 2, 2018, 9 pages (for reference purposes only).

* cited by examiner

*Primary Examiner* — Joseph R Kosack
(74) *Attorney, Agent, or Firm* — Viering Jentschura & Partner MBB

(57) ABSTRACT

A detergent, cleaning, fabric softener or cosmetic composition comprising a compound based on 1-Aza-3,7-dioxabicyclo[3.3.0]octane (bicyclic oxazolidine derivative) substituted with 3,7-dimethyl-1,6-nonyldien represented by formula (I)

(I)

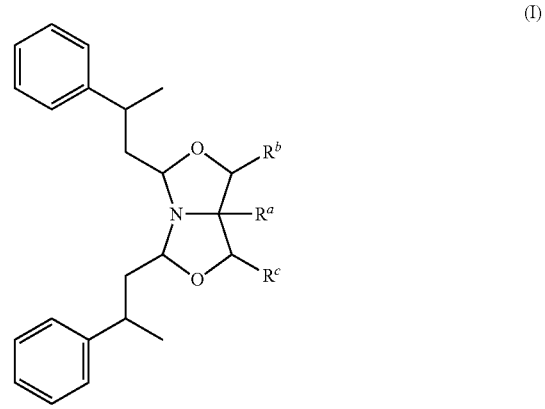

is disclosed.

19 Claims, No Drawings

COMPOSITIONS COMPRISING PRECURSORS FOR VOLATILES

CROSS-REFERENCE TO RELATED APPLICATIONS

The present application is a national stage entry according to 35 U.S.C. § 371 of PCT application No.: PCT/EP2018/075921 filed on Sep. 25, 2018; which claims priority to German Patent Application Serial No.: 10 2017 122 977.9, which was filed on Oct. 4, 2017; which is incorporated herein by reference in its entirety and for all purposes.

TECHNICAL FIELD

A detergent, cleaning, fabric softener or cosmetic compositions may include a compound based on 1-Aza-3,7-dioxabicyclo[3.3.0]octane (bicyclic oxazolidine derivative) substituted with 2-phenyl propyl.

BACKGROUND

In addition to the use of fragrances in detergent, cleaning, fabric softening and cosmetic composition, it is also known to use pro-fragrances in such compositions. By analogy with pro-drugs, pro-fragrances are chemical derivatives of a fragrance, which for example reduce the volatility of the fragrance and allow a delayed release of the fragrance over time under ambient conditions. By derivatization of fragrances, such as aldehyde or ketone fragrances, the vapor pressure of these compounds can be lowered. Since the derivatization reaction is reversible, the chemically bound aldehyde or ketone fragrance may, under certain conditions, e.g., ambient conditions, be released, which may lead to a prolonged scent impression.

The base compound used for forming the pro-fragrance is a 1-aza-3,7-dioxabicyclo[3.3.0]octane (bicyclic oxazolidine derivative). Such oil-soluble substituted monocyclic and bicyclic oxazolidines are disclosed for the use as additives in automatic transmission fluids, for example, in U.S. Pat. No. 4,277,353. Examples described therein include reaction products of optionally substituted 2-amino-1,3-propanediols with paraformaldehyde and isobutyraldehyde.

Pro-fragrance compounds based on 1-aza-3,7-dioxabicyclo[3.3.0]octane derivatives are for example disclosed in WO 2007/087977 A1. In this reference, a generic formula for those compounds is disclosed together with a long list of exemplary compounds for aldehydes or ketones that are commonly used as fragrances.

An object of the present invention was to provide detergent, cleaning, fabric softener or cosmetic compositions comprising oxazolidine compounds of the general formula of WO 2007/087977 A1, that provide for a prolonged scent perception, in particular in comparison to the explicitly disclosed examples of this reference.

SUMMARY

The present inventors have surprisingly found that 1-aza-3,7-dioxabicyclo[3.3.0]octane (bicyclic oxazolidine derivatives) compounds substituted with 2-phenylpropyl, produced by reacting the corresponding aldehyde 3-methyl-3-phenylpropanal (commercially available under the tradename trifernal) with serinol or a derivative thereof, provide for improved scent long-lastingness and intensity compared to other known 1-aza-3,7-dioxabicyclo[3.3.0]octane compounds, for example those substituted with 3-(4-tert-butylphenyl)-2-methylpropyl (using the corresponding aldehyde 3-(4-tert-butylphenyl)-2-methylpropanal In a first aspect, the present invention thus relates to detergent, cleaning, fabric softener or cosmetic composition comprising a compound based on 1-Aza-3,7-dioxabicyclo[3.3.0]octane substituted with 2-phenylpropyl represented by formula (I)

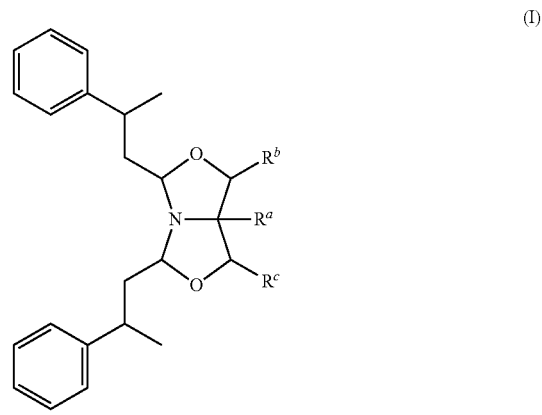

wherein $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen.

In a second aspect, the invention pertains to detergent, cleaning, fabric softener or cosmetic composition comprising a mixture of at least one compound of formula (I) and at least one compound of formula (II)

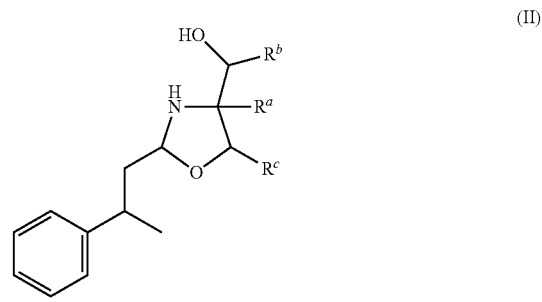

wherein $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen.

The invention also relates to a method for prolonging the scent of detergent, cleaning, fabric softening or cosmetic compositions or surfaces, in particular hard surfaces treated with those compositions, wherein said compositions are those described herein and comprise at least one compound of formula (I) or mixtures of the compounds of formulae (I) and (II). In particular, the scent impression is prolonged compared to using the compound of formula (IV).

DETAILED DESCRIPTION

"One or more", as used herein, relates to at least one and comprises 1, 2, 3, 4, 5, 6, 7, 8, 9 or more of the referenced species. Similarly, "at least one" means one or more, i.e. 1, 2, 3, 4, 5, 6, 7, 8, 9 or more. "At least one", as used herein in relation to any component, refers to the number of chemically different molecules, i.e. to the number of different types of the referenced species, but not to the total number of molecules. For example, "at least one aldehyde" means that at least one type of molecule falling within the definition for an aldehyde is used but that also two or more different molecule types falling within this definition can be present, but does not mean that only one molecule of said aldehyde is present.

If reference is made herein to a molecular weight, this reference refers to the weight average molecular weight $M_w$, if not explicitly stated otherwise. The weight average molecular weight can be determined by gel permeation chromatography.

All percentages given herein in relation to the compositions or formulations relate to weight % relative to the total weight of the respective composition or formula, if not explicitly stated otherwise.

In a non-limiting embodiment, detergent, cleaning, fabric softening and cosmetic compositions are also referred to as agents, such as, e.g., detergent agent or fabric softening agent.

It has been surprisingly found by the inventors that compounds based on 1-aza-3,7-dioxabicyclo[3.3.0]octane substituted with 2-phenylpropyl have an improved prolonged scent impression compared to the compounds of this type known in the prior art. Furthermore, it has been found that the deposition of such bicyclic compounds on solid surfaces such as textiles, skin or hard surfaces is improved.

The compounds of formulae (I) and (II) used in the compositions can be obtained by a method that comprises reacting at least one compound of formula (III)

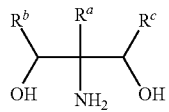
(III)

wherein $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen; with

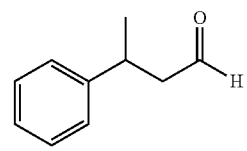
(IV)

a compound of formula (IV)

in a ring forming reaction. In this reaction, the aldehyde group of 3-methyl-3-phenylpropanal reacts with the hydroxyl and the amino groups of the compound of formula (III) to form the compounds of formula (I) and/or (II).

The compounds of general formula (III) are derived from 2-amino-1,3-propanediol (serinol). By producing the bicyclic compounds, it is possible to achieve a high degree of loading of the 2-amino-1,3-propanediols, so that the use of smaller amounts of 2-amino-1,3-propanediols is possible. This achieves a prolongation of the scent impression even with smaller amounts of 2-amino-1,3-propanediols, which can lead to cost advantages and also avoids the introduction of large quantities of chemicals into detergent, cleaning, fabric softening or cosmetic compositions.

As can be seen from the above, it is also possible to use monocyclic compounds based on 2-amino-1,3-propanediols, i.e. the compounds of formula (II). These are generated as byproducts in the synthesis of the compounds of formula (I). It is possible to achieve a high degree of loading of the 2-amino-1,3-propanediols, so that bicyclic oxazolidines are generally used.

In compounds according to formula (I) $R^a$ is hydrogen or a $C_{1-20}$ alkyl group which can optionally be substituted with hydroxyl groups and/or amine groups and/or in which up to 8 —$CH_2$— groups which are not adjacent to each other can be substituted by —O—, such as $R^a$ is hydrogen or $C_{1-6}$ alkyl, alternatively $R^a$ is hydrogen or methyl, or $R^a$ is hydrogen;

$R^b$ and $R^c$ are independently selected from hydrogen or $C_{1-6}$ alkyl, such as $R^b$ and $R^c$ are independently selected from hydrogen and methyl, alternatively $R^b$ and $R^c$ are both hydrogen.

In various embodiments, $R^a$ is hydrogen or methyl and $R^b$ and $R^c$ are hydrogen. Non-limiting embodiments include $R^a$ to $R^c$ to both be hydrogen. In another non-limiting embodiment, $R^a$ is methyl and $R^b$ and $R^c$ are hydrogen. This provides for an improved long-lastingness of the scent and high intensity even after prolonged periods of time.

To produce the compounds of formula (I) the amino alcohol of formula (III) is reacted with an aldehyde of formula (IV) which is 4,8-dimethyl-4,9-decadienal, commercially available under the name floral super and having the CAS No. 71077-31-1. According to one embodiment, the compounds of general formula (I) are derived from a 2-amino-1,3-propanediol molecule of formula (III) and two aldehyde molecules of formula (IV). In the reaction of less than stoichiometric amounts of aldehydes, monocyclic compounds are also present in the product mixture. The amount of bicyclic compounds to monocyclic compounds may be adjusted easily through the choice of the molar ratios between aldehyde and 2-amino-1,3-propanediol. Large amounts of bicyclic structures are especially useful. Such mixtures contain at least 50 wt.-%, such as at least 65 wt.-%, or at least 80 wt.-% of bicyclic structures, based on the total weight of the compounds. In various embodiments, this means that in the mixtures of compounds according to formulae (I) and (II), the amount of compounds of formula (I) is higher than 50 mol.-% relative to the total amount of compounds of formulae (I) and (II), such as higher than 70 mol.-%, alternatively higher than 80 mol.-%, or at least 90 mol.-%.

The reaction is performed in a suitable solvent or in situ, such as in a suitable solvent. Suitable solvents include, for example, hydrocarbons containing aromatics, in particular toluene. The reaction is carried out at a temperature in the range of 80 to 150° C., such as 100 to 140° C., alternatively at 120° C. For example, as the starting material the compound of general formula (III) is used together with the aldehyde and the solvent under nitrogen atmosphere. This reaction mixture is then heated, such as from 5 minutes to 20 hours, alternatively from 1 to 10 hours, or from 6 to 8 hours, whereupon the solids gradually go into solution. The reaction is finished when no more water as by-product of the reaction is produced. The mixture is heated under reflux on a water separator. The resulting reaction product is isolated by conventional methods, for example by drying in vacuum, and purified if necessary.

The compounds are used as pro-fragrances. The term "pro-fragrance" describes in general derivatives of aldehyde and ketone fragrances, which release the original aldehydes and ketones under ambient conditions. Ambient conditions are typical ambient conditions in the human biosphere and/or the conditions encountered on human skin. The compounds of general formula (I) and (II) disintegrate slowly under ambient conditions in a reversal of the synthesis process, releasing the original aldehydes. Accordingly, the compounds may be used as pro-fragrances.

The at least one compound may be used as the only fragrance substance, but it is also possible to use mixtures of fragrances, which are comprised only partially of the at least one compound. In particular, fragrance mixtures containing 1 to 50 wt.-%, such as 5 to 40.-wt.-%, and in particular max. 30 wt.-% of the at least one compound of formula (I) or the mixture of compounds of formulae (I) and (II), based on the total weight of the fragrance mixture may be used. In a non-limiting embodiment, the at least one compound or compound mixture can be used together with further fragrance compounds different from the compounds of formulae (I) and (II). By the use of additional perfume compounds in the compositions, e.g., detergent or cleaning compositions, it is possible to create a variety of characteristics of the final product, which are only possible by using them in combination with the at least one compound or the mixture of the compounds. For example, it is possible to divide the total perfume content (fragrance content) of a composition, for example a detergent or cleaning composition, into two portions, x and y, wherein portion x comprises the compounds and portion y comprises traditional scent substances, like perfume oils.

The fragrance substances (or perfume compounds, with these two terms being used interchangeably herein) that may be additionally incorporated are not subject to any restrictions. Individual perfume substance compounds of natural or synthetic origin, e.g., of the type of esters, ethers, aldehydes, ketones, alcohols and hydrocarbons may thus be used as the perfume substance including perfume oils. Fragrance compounds of the ester type include, for example, benzyl acetate, phenoxyethyl isobutyrate, p-tert-butylcyclohexyl acetate, linalyl acetate, dimethylbenzylcarbinyl acetate (DMBCA), phenylethyl acetate, benzyl acetate, ethylmethyl phenyl glycinate, allylcyclohexyl propionate, styrallyl propionate, benzyl salicylate, cyclohexylsalicylate, floramat, melusat and jasmacyclate. The ethers include, for example, benzylethyl ether and ambroxan; the aldehydes include, for example, the linear alkanals with 8 to 18 carbon atoms, citral, citronellal, citronellyl oxyacetaldehyde, cyclamenaldehyde, lilial and bourgeonal; the ketones include, for example, the ionones, α-isomethylionone and methyl cedryl ketone; the alcohols include anethole, citronellol, eugenol, geraniol, linalool, phenylethyl alcohol and terpineol; the hydrocarbons include mainly terpenes such as limonene and pinene. However, mixtures of various fragrance substances which jointly produce an attractive scent note are possible.

Such fragrance substances may also contain mixtures of natural perfume substances such as those accessible from plant sources, e.g., pine oil, citrus oil, jasmine oil, patchouli oil, rose oil or ylang-ylang oil. Also suitable are muscatel sage oil, chamomile oil, clove oil, lemon balm oil, mint oil, cinnamon leaf oil, linden blossom oil, juniper berry oil, vetiver oil, olibanum oil, galbanum oil and labdanum oil as well as orange blossom oil, neroli oil, orange peel oil and sandalwood oil.

Other traditional fragrance substances that may be used include, for example, the essential oils such as angelica root oil, anise oil, arnica blossom oil, sweet basil oil, bay oil, champaca blossom oil, silver fir oil, fir cone oil, elemi oil, eucalyptus oil, fennel oil, spruce needle oil, galbanum oil, geranium oil, ginger grass oil, guaiac wood oil, gurjun balsam oil, helichrysum oil, ho oil, ginger oil, iris oil, cajeput oil, calamus oil, chamomile oil, camphor oil, canaga oil, cardamom oil, cassia oil, pine needle oil, copaiba balsam oil, coriander oil, spearmint oil, caraway oil, cumin oil, lavender oil, lemon grass oil, lime oil, mandarin oil, lemon balm oil, ambrette seed oil, myrrh oil, clove oil, neroli oil, niaouli oil, olibanum oil, origanum oil, palmarosa oil, patchouli oil, Peru balsam oil, petitgrain oil, pepper oil, peppermint oil, allspice oil, pine oil, rose oil, rosemary oil, sandalwood oil, celery seed oil, spike lavender oil, star anise oil, turpentine oil, thuja oil, thyme oil, verbena oil, vetiver oil, juniper berry oil, vermouth oil, wintergreen oil, ylang-ylang oil, ysop oil, cinnamon oil, cinnamon leaf oil, citronella oil, lemon oil and cypress oil as well as compounds selected from the group of ambrettolide, ambroxan, α-amylcinnamaldehyde, anethole, anise aldehyde, anise alcohol, anisole, anthranilic acid methyl ester, acetophenone, benzylacetone, benzaldehyde, benzoic acid ethyl ester, benzophenone, benzyl alcohol, benzyl acetate, benzyl benzoate, benzyl formate, benzyl valerate, borneol, bornyl acetate, boisambrene forte, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptin carboxylic acid methyl ester, heptaldehyde, hydroquinone dimethyl ester, hydroxycinnamyl aldehyde, hydroxycinnamyl alcohol, indole, iron, isoeugenol, isoeugenol methyl ether, isosafrol, jasmine, camphor, carvacrol, carbon, p-cresol methyl ether, coumarin, p-methoxyacetophenone, methyl-n-amyl ketone, methyl anthranilic acid methyl ester, p-methylacetophenone, methyl chavicol, p-methylquinoline, methyl β-naphthyl ketone, methyl n-nonylaldehyde, nonyl alcohol, n-octylaldehyde, p-oxyacetphenone, pentadecanolide, β-phenylethyl alcohol, phenylacetaldehyde-dimethylacetal, phenylacetic acid, pulegon, safrole, salicylic acid isoamyl ester, salicylic acid methyl ester, salicylic acid hexyl ester, salicylic acid cyclohexyl ester, santalol, sandelice, skatol, terpineol, thyme, thymol, troenan, γ-undelactone, vanillin, veratrum aldehyde, cinnamyl aldehyde, cinnamyl alcohol, cinnamic acid, cinnamic acid ethyl ester, cinnamic acid benzyl ester, diphenyl oxide, limonene, linalool, linyl acetate and linalyl propionate, melusat, menthol, menthone, methyl-n-heptenone, pinene, phenyl acetaldehyde, terpinyl acetate, citral, citronellal and mixtures thereof.

All fragrance substances disclosed herein, can be used in the compositions or agents in free or encapsulated form or both. Specifically, the compounds of formulae (I) and (II) can be used in free or encapsulated form or both. As they are used as precursors, they are used in free, i.e. non-encapsulated form. In various embodiments, they can be combined with encapsulated fragrances, wherein these may also include free nympheal. As capsules, microcapsules can be used, all of which are known in the art and include, without limitation, aminoplast and acrylate microcapsules. The microcapsules in which the fragrances or pro-fragrances are encapsulated may have a core-shell morphology, with the shell being typically formed of a polymer, or alternatively may have the form of matrix particles in which the fragrance substances are entrapped.

The at least one compound of formula (I) or the mixture of compounds of formulae (I) and (II) can be used in perfume compositions, can be present in those in amounts of 0.001 to 100 wt.-% relative to the total weight of the perfume composition, such as in amounts of 0.1 to 90 wt.-%, such as 1 to 90 wt.-%, 2 to 85 wt.-%, 5 to 75 wt.-% or 10 to 50 wt.-%.

The at least one compound of formula (I) or the mixture of compounds of formulae (I) and (II) are used in detergents and cleaning compositions, fabric softening composition and cosmetic compositions. These may be solid, gel or liquid formulations, and solid formulations may be in the form of powder, granules, tablets or tabs. Liquid formulations may be solutions, emulsions or dispersions. A mixture of those can be present as well, for example in one dosage unit systems comprising two or three different forms, like pouches. For example, such dosage forms can include solid and liquid compositions, or solid and gel or liquid and gel or all three.

Detergent compositions can in particular be used for manual or machine washing of textiles. They may be detergents or cleaning compositions for industrial use or for domestic use. Cleaning compositions are those used for cleaning hard surfaces. Such compositions include dishwashing detergents, which are used for manual dishwashing or automatic dishwashers. Also included are conventional industrial or household cleaners with which hard surfaces such as furniture surfaces, flagstones, ceramic tiles, wall coverings and floor coverings are cleaned. Fabric softening compositions include, in particular, fabric softeners that are used for treating textiles during or after being laundered. The cosmetic compositions may be pastes, ointments, creams, emulsions, lotions and solutions, in particular, alcohol-based solutions, which are known from fine perfumery, for example. The individual agents may be applied in any suitable form. For example, they can be applied by spraying. The inventive compounds and mixtures may also be used to cover bad odors, which adhere well to solid surfaces when combined with other absorbents, for example.

The detergent, cleaning, fabric softening or cosmetic compositions, may comprise the at least one inventive compound of formula (I) or mixtures of the compounds of formula (I) and (II). The compounds or mixtures are used in an amount sufficient for the effect. In non-limiting embodiments the detergent, cleaning, fabric softener or cosmetic compositions comprise the at least one compound or compound mixture in amounts of 0.000001 to 5 wt.-%, such as 0.00001 to 2 wt.-%, alternatively 0.0001 to 1 wt.-%, or in 0.0001 to 0.1 wt.-%, based on the total weight of the composition.

Those skilled in the art are familiar with the composition of conventional detergents or cleaning agents, fabric softeners and cosmetics and can design such agents based on their common technical knowledge.

Detergents and cleaning agents and fabric softeners may contain other conventional ingredients of detergents and cleaning and fabric softeners, such as surfactants, builder substances, bleaching agents, other scent substances, enzymes and other active ingredients, but also disintegration aids, tablet disintegrants, to facilitate the disintegration of highly compressed tablets and tabs and to shorten the disintegration times. Surfactants, in particular, are among the essential ingredients of detergents and cleaning agents and fabric softeners.

A high or low surfactant content will be selected, depending on the intended use of the inventive agents. The surfactant content of a detergent agent is usually between 10 and 40 wt.-%, such as between 12.5 and 30 wt.-% and, in particular, between 15 and 25 wt.-%, whereas cleaning agents for dishwashing machines contain between 0.1 and 10 wt.-%, such as between 0.5 and 7.5 wt.-% and, in particular, between 1 and 5 wt.-% surfactant, based on the total weight of the respective detergent or cleaning agent.

The surfactants are typically selected from the group of anionic, nonionic, zwitterionic or cationic surfactants but for economic reasons and because of their performance spectrum, anionic and/or nonionic surfactants are usable in washing and cleaning compositions, while in fabric softening compositions, cationic surfactants are used.

In principle, all anionic surfactant substances suitable for use on the human body may be used as the anionic surfactants. These are characterized by a water-solubilizing anionic group, e.g., a carboxylate, sulfate, sulfonate or phosphate group and a lipophilic alkyl group with approximately 8 to 30 carbon atoms. In addition, glycol or polyglycol ether groups, ester, ether and amide groups as well as hydroxyl groups may be present in the molecule. Examples of suitable anionic surfactants include the following, and can be in the form of a sodium, potassium and/or ammonium salt, as well as the mono-, di- and trialkanolammonium salts with 2 to 4 carbon atoms in the alkanol group as well:

linear and branched fatty acids having the formula $R^1$—COOH, wherein $R^1$ is an linear or branched $C_8$ to $C_{30}$ alkyl (soaps), ether carboxylic acids of formula $R^2$—O—($CH_2$—$CH_2O$)$_x$—$CH_2$—COOH, in which $R^2$ is a linear alkyl group with 8 to 30 carbon atoms and x=0 or 1 to 16, alkylsarcosides with 8 to 24 carbon atoms in the acyl group, acyltaurides with 8 to 24 carbon atoms in the acyl group, acylsethionates with 8 to 24 carbon atoms in the acyl group, sulfosuccinic acid monoalkyl and dialkyl esters with 8 to 24 carbon atoms in the alkyl group and sulfosuccinic acid monoalkylpolyoxyethyl esters with 8 to 24 carbon atoms in the alkyl group and 1 to 6 oxyethyl groups, linear alkanesulfonates with 8 to 24 carbon atoms, linear α-olefinsulfonates with 8 to 24 carbon atoms, α-sulfofatty acid methyl esters of fatty acids with 8 to 30 carbon atoms, alkyl sulfates and alkypolyglycol ether sulfates of formula $R^3$—O($CH_2$—$CH_2O$)$_x$—$OSO_3H$, in which $R^3$ is a alkyl group, such as a linear alkyl group, with 8 to 30 carbon atoms and x=0 or 1 to 12, mixed surfactant hydroxysulfonates,
sulfated hydroxyalkylpolyethylene and/or hydroxyalkylenepropylene glycol ethers,
sulfonated unsaturated fatty acids with 8 to 24 carbon atoms and 1 to 6 double bonds,
esters of tartaric acid and citric acid with alcohols which are addition products of approximately 2 to 15 molecules of ethylene oxide and/or propylene oxide onto fatty alcohols with 8 to 22 carbon atoms,
alkyl and/or alkenyl ether phosphates of the formula (E1-I):

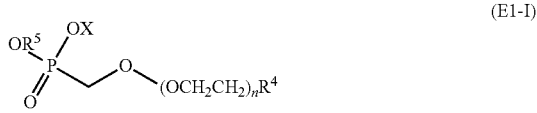

(E1-I)

in which $R^4$ is an aliphatic hydrocarbon radical with 8 to 30 carbon atoms, $R^5$ is hydrogen, a $(CH_2CH_2O)_nR^6$, wherein $R^6$ is an aliphatic hydrocarbon radical with 8 to 30 carbon atoms, group or X, n is an integer from 1 to 10 and X is independently hydrogen an alkali metal or an alkaline earth metal or a $NR^7R^8R^9R^{10}$ group, with $R^7$ to $R^{10}$ being indepently selected from hydrogen or a C1 to C4 hydrocarbon radical,
sulfated fatty acid alkylene glycol esters of formula (E1-II):

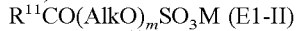

in which $R^{11}CO$— is a linear or branched, aliphatic, saturated and/or unsaturated acyl radical with 6 to 22 carbon atoms, Alk is $CH_2CH_2$, $CHCH_3CH_2$ and/or $CH_2CHCH_3$, m is a number from 0.5 to 5 and M is a cation,
monoglyceride sulfates and monoglyceride ether sulfates of formula (E1-III)

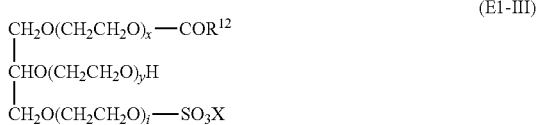

(E1-III)

in which $R^{12}CO$ is a linear or branched acyl radical with 6 to 22 carbon atoms, x, y and i add up to 0 or stand for numbers from 1 to 30, such as 2 to 10, and X stands for an alkali metal or an alkaline earth metal. Typical examples of monoglyceride (ether) sulfates suitable include the reaction products of lauric acid monoglyceride, coconut fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid in the form of their sodium salts. Monoglyceride sulfates of formula (E1-II) are used in which $R^{12}CO$ is a linear acyl radical with 8 to 18 carbon atoms,
amide ether carboxylic acids,
condensation products of C8-C30 fatty alcohols with protein hydrolysates and/or amino acids and their derivatives with which those skilled in the art are familiar as protein-fatty acid condensates such as Lamepon® grades, Gluadin® grades, Hostapon® KCG or the Amisoft® grades.
Non-limiting anionic surfactants include alkyl sulfates, alkylpolyglycol ether sulfates and ether carboxylic acids with 10 to 18 carbon atoms in the alkyl group and up to 12 glycol ether groups in the molecule, sulfosuccinic acid monoalkyl and dialkyl esters with 8 to 18 carbon atoms in the alkyl group and sulfosuccinic acid monoalkylpolyoxyethyl esters with 8 to 18 carbon atoms in the alkyl group and 1 to 6 oxyethyl groups, monoglyceride sulfates, alkyl and alkenyl ether phosphates and protein-fatty acid condensates. In non-limiting embodiments those anionic surfactants are present in 1 to 20 wt.-%, such as 3 to 15 wt.-%, based on the total weight of the composition.

Cationic surfactants may also be used. Non-limiting cationic surfactants of the quaternary ammonium compound type include, ester quats and amidoamines. Non-limiting quaternary ammonium compounds include ammonium halides, in particular, chlorides and bromides such as alkyltrimethylammonium chlorides, dialkyldimethylammonium chlorides and trialkylmethylammonium chloride, e.g., cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, lauryldimethylammonium chloride, lauryldimethylbenzylammonium chloride and tricetylmethylammonium chloride as well as the imidazolium compounds known by the INCI designations quaternium-27 and quaternium-83 are usable. The long alkyl chains of the surfactants mentioned above may have 10 to 18 carbon atoms.

Ester quats are known substances which contain at least one ester function as well as at least one quaternary ammonium group as a structural element. Non-limiting ester quats are quaternated ester salts of fatty acids with triethanolamine, quaternated ester salts of fatty acids with diethanolalkylamines and quaternated ester salts of fatty acids with 1,2-dihydroxypropyldialkylamines. Such products are distributed under the brand names Stepantex®, Dehyquart® and Armocare®, for example. The products Armocare® VGH-70, and N,N-bis(2-palmitoyloxyethyl)dimethylammonium chloride as well as Dehyquart® F-17, Dehyquart® C-4046, Dehyquart® L80 and Dehyquart® AU-35 are commercially available examples of such esterquats.

The alkylamidoamines are usually prepared by amidation of natural or synthetic fatty acids and fatty acid cuts with dialkylaminoamines. Stearamidopropyldimethylamine, which is available commercially under the brand name Tegoamid® S18 is an especially suitable compound.

The cationic surfactants are present in the inventive agents in amounts of 0.05 to 10 wt.-%, based on the total weight of the respective composition. Amounts of 0.1 to 5 wt.-% are used.

In addition to or instead of the cationic surfactants, the agents may also contain other surfactants or emulsifiers, in principle, both anionic and ampholytic and nonionic surfactants as well as all types of known emulsifiers being suitable. The group of ampholytic or amphoteric surfactants comprises zwitterionic surfactants and ampholytes. The surfactants may already have an emulsifying effect.

Zwitterionic surfactants are surfactant compounds having at least one quaternary ammonium group and at least one —COO$^{(-)}$ oder —SO$_3^{(-)}$-group. Especially suitable zwitterionic surfactants include betaines such as N-alkyl-N,N-dimethylammonium glycinates, e.g., the coconut alkyldimethylammonium glycinate, N-acylaminopropyl-N,N-dimethylammonium glycinates, e.g., coconut acylaminopropyldimethylammonium glycinate and 2-alkyl-3-carboxymethyl-3-hydroxyethylimidazolines with 8 to 18 carbon atoms each in the alkyl or acyl group as well as coconut acylaminoethylhydroxyethylcarboxymethyl glycinate. A non-limiting zwitterionic surfactant is the fatty acid amide derivative known by the INCI name cocamidopropyl betaine.

Ampholytes are understood to be surfactant compounds which have, in addition to a $C_8$-$C_{24}$ alkyl or acyl group in the molecule, at least one free amino group and at least one —COOH or —SO3H group and are capable of forming internal salts. Examples of suitable ampholytes include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkyl-sarcosines, 2-alkylaminopropionic acids and alkylaminoacetic acids each with approx. 8 to 24 carbon atoms in the alkyl group. Non-limiting examples of ampholytes include N-coconut alkylaminopropionate, coconut acylaminoethylaminopropionate and $C_{12}$-$C_{18}$ acylsarcosine.

Nonionic surfactants contain as the hydrophilic group, e.g., a polyol group, a polyalkylene glycol ether group or a combination of a polyol group and a polyglycol ether group. Such compounds include, for example:

addition products of 2 to 50 mol ethylene oxide and/or 1 to 5 mol propylene oxide onto linear and branched fatty alcohols with 8 to 30 carbon atoms, onto fatty acid with 8 to 30 carbon atoms and onto alkylphenols with 8 to 15 carbon atoms in the alkyl group, with a methyl- or $C_2$-$C_6$ alkyl radical end group capped addition products of 2 to 50 mol ethylene oxide and/or 1 to 5 mol propylene oxide onto linear and branched fatty alcohols with 8 to 30 carbon atoms, onto fatty acids with 8 to 30 carbon atoms and onto alkylphenols with 8 to 15 carbon atoms in the alkyl group such as the grades available under the brand names Dehydol® LS, Dehydol® LT (BASF), $C_{12}$-$C_{30}$ fatty acid mono- and diesters of addition products of 1 to 30 mol ethylene oxide onto glycerol, addition products of 5 to 60 mol ethylene oxide onto castor oil and hardened castor oil, polyol fatty acid esters such as the commercial product Hydagen® HSP (BASF) or Sovermol grades (BASF), alkoxylated triglycerides, alkoxylated fatty acid alkyl esters of formula (E1-IV)

$$R^{13}CO-(OCH_2CHR^{14})_wOR^{15} \qquad \text{(E1-IV)}$$

in which $R^{13}CO$ is fa linear or branched, saturated and/or unsaturated acyl radical with 6 to 22 carbon atoms, $R^{14}$ is hydrogen or methyl, $R^{15}$ is linear or branched alkyl radicals with 1 to 4 carbon atoms and w stands for numbers from 1 to 20, amine oxides, hydroxy mixed ethers, sorbitan fatty acid esters and addition products of ethylene oxide onto sorbitan fatty acid esters such as the polysorbates, sugar fatty acid esters and addition products of ethylene oxide onto sugar fatty acid esters, addition products of ethylene oxide onto fatty acid alkanolamides and fatty amines, sugar surfactants of the alkyl and alkenyl oligoglycoside type according to formula (E1-V)

$$R^{16}O-[G]_p \qquad \text{(E1-V)}$$

in which $R^{16}$ is an alkyl or alkenyl radical with 4 to 22 carbon atoms, G stands for a sugar radical with 5 or 6 carbon atoms and p stands for numbers from 1 to 10. They may be obtained according to the relevant methods or preparative organic chemistry. The alkyl and alkenyl oligoglycosides may be derived from aldoses and/or ketoses with 5 or 6 carbon atoms, such as glucose. The alkyl and/or alkenyl oligoglycosides are thus alkyl and alkenyl oligoglucosides. The index number p in the general formula (E1-V) denotes the degree of oligomerization (DP), i.e., the distribution of mono- and oligoglycosides, and stands for a number between 1 and 10. Whereas p in the individual molecule must always be an integer and may assume values of p=1 to 6, in particular, the value p for a certain alkyl oligoglycoside is a mathematical quantity obtained analytically and usually representing a fraction. Alkyl and/or alkenyl oligoglycosides with an average degree of oligomerization p of 1.1 to 3.0 are used. From the standpoint of technical applications, alkyl and/or alkenyl oligoglycosides whose degree of oligomerization is less than 1.7 and, in particular, between 1.2 and 1.4 are used. The alkyl and/or alkenyl radical $R^{16}$ may be derived from primary alcohols with 4 to 11 carbon atoms, such as 8 to 10 carbon atoms. Typical examples include butanol, caproic alcohol, caprylic alcohol, capric alcohol and undecyl alcohol as well as their technical-grade mixtures such as those obtained, e.g., in hydrogenation of technical-grade fatty acid methyl esters or in the course of hydrogenation of aldehydes from the Roelen oxo synthesis. Alkyl oligoglucosides with a chain length of $C_8$-$C_{10}$ (DP=1 to 3), which are obtained as the initial fraction in distillative separation of technical-grade $C_8$-$C_{18}$ coconut fatty alcohol and which may be contaminated with an amount of less 6 wt.-% $C_{1-2}$ alcohol, as well as alkyl oligoglucosides based on technical-grade $C_{9/11}$ oxo alcohols (DP=1 to 3) are used. The alkyl and/or alkenyl radical $R^{16}$ can as well derived from primary alcohols with 12 to 22 carbon atoms, such as 12 to 14 carbon atoms. Typical examples include lauryl alcohol, myristyl alcohol, cetyl alcohol, palmoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol as well as their technical-grade mixtures which are obtained by the method described above. Alkyl oligoglucosides based on hardened $C_{12/14}$ coconut alcohol with a DP of 1 to 3 are used.

Sugar surfactants of the fatty acid N-alkylpolyhydroxyalkylamide type, a nonionic surfactant of the formula (E1-VI)

(E1-VI)

in which $R^{18}CO$ is an aliphatic acyl radical with 6 to 22 carbon atoms, $R^{17}$ hydrogen, an alkyl or hydroxyalkyl radical with 1 to 4 carbon atoms and [Z] is a linear or branched polyhydroxyalkyl radical with 3 to 12 carbon atoms and 3 to 10 hydroxyl groups. The fatty acid N-alkylpolyhydroxyalkylamides are known substances which can usually be obtained by reductive amination of a reducing sugar with ammonia, an alkylamine or an alkanolamine and subsequent acylation with a fatty acid, a fatty acid alkyl ester or a fatty acid chloride. The fatty acid N-alkylpolyhydroxyalkylamides are derived from reducing sugars with 5 or 6 carbon atoms, in particular glucose.

The fatty acid N-alkylpolyhydroxyalkylamides are therefore fatty acid N-alkylglucamides such as those represented by formula (E1-VII):

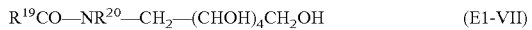

$$R^{19}CO-NR^{20}-CH_2-(CHOH)_4CH_2OH \qquad \text{(E1-VII)}$$

The fatty acid N-alkylpolyhydroxyalkylamides used are glucamides of the formula (E1-VII) in which $R^{20}$ is hydrogen or an alkyl group and $R^{19}CO$ is an acyl group of caproic acid, caprylic acid, capric acid, lauric acid, myristic acid, palmitic acid, palmoleic acid, stearic acid, isostearic acid, oleic acid, elaidic acid, petroselinic acid, linoleic acid, linolenic acid, arachic acid, gadoleic acid, behenic acid or erucaic acid and/or technical-grade mixtures of these acids. Non-limiting examples of fatty acid N-alkylglucamides are those of formula (E1-VII) that are obtained by reductive amination of glucose with methylamine and then acylation with lauric acid or $C_{12/14}$ coconut fatty acid and/or a corresponding derivative. In addition, the polyhydroxy-alkylamides may also be derived from maltose and palatinose.

Non-limiting examples of nonionic surfactants are alkylene oxide addition products onto saturated linear fatty alcohols and fatty acids each with 2 to 30 mol ethylene oxide per mol fatty alcohol and/or fatty acid. Preparations with excellent properties are also obtained when they contain fatty acid esters of ethoxylated glycerol as the nonionic surfactants.

These compounds are characterized by the following parameters. The alkyl radical contains 6 to 22 carbon atoms and may be both linear and branched. Primary linear aliphatic radicals and those with methyl branching in position 2 are used. Such alkyl radicals include 1-octyl, 1-decyl, 1-lauryl, 1-myristyl, 1-cetyl and 1-stearyl. When using "oxo alcohols" as the starting materials, compounds with an odd number of carbon atoms in the alkyl chain are predominant.

In addition, the sugar surfactants may also be used as nonionic surfactants. These are used in amounts of 0.1 to 20 wt.-%, based on the respective total composition. Amounts of 0.5 to 15 wt.-% are used and amounts of 0.5 to 7.5 wt.-% are possible.

The compounds with alkyl groups that are used as the surfactant may be uniform substances. However, it is preferable as a rule to start with native plant or animal raw materials in the production of these substances, so that substance mixtures with different alkyl chain lengths are obtained, depending on the respective raw material.

The surfactants, which are addition products of ethylene oxide and/or propylene oxide onto fatty alcohols or derivatives of these addition products, may be products with a "normal" homolog distribution as well as those with a narrow homolog distribution. A "normal" homolog distribution is understood to refer to mixtures of homologs that are obtained by reacting fatty alcohol and alkylene oxide using alkali metals, alkali metal hydroxides or alkali metal alcoholates as catalysts. Narrow homolog distributions, however, are obtained when using, for example, hydrotalcite, alkaline earth metal salts of ether carboxylic acids, alkaline earth metal oxides, hydroxides or alcoholates as catalysts. The use of products with a narrow homolog distribution may be used.

These nonionic surfactants are usually used in amounts of 0.1 to 45 wt.-%, such as 0.5 to 30 wt.-% or from 0.5 to 25 wt.-%, each based on the respective total composition. The amount used depends essentially on the intended purpose of the inventive agent. If it is a shampoo or another cleaning agent, surfactant amounts of more than 45 wt.-%.

The compositions may also contain at least one emulsifier. Emulsifiers cause the formation of water-stable and/or oil-stable adsorption layers at the phase boundary, protecting the dispersed droplets from coalescence and thereby stabilizing the emulsion. Emulsifiers are therefore composed of a hydrophobic molecule part and a hydrophilic molecule part, like surfactants. Hydrophilic emulsifiers form O/W emulsions and hydrophobic emulsifiers form W/O emulsions. The choice of these emulsifying surfactants or emulsifiers will depend on the substances to be dispersed and the particular external phase, as well as how finely divided the emulsion is.

Emulsifiers that can be used include, for example:

addition products of 4 to 100 mol ethylene oxide and 1 to 5 mol propylene oxide onto linear fatty alcohols with 8 to 22 carbon atoms onto fatty acids with 12 to 22 carbon atoms and onto alkylphenols with 8 to 15 carbon atoms in the alkyl group, $C_{12}$-$C_{22}$ fatty acid mono- and diesters of addition products of 1 to 30 mol ethylene oxide onto polyols with 3 to 6 carbon atoms, in particular onto glycerol, ethylene oxide and polyglycerol addition products onto methyl glucoside fatty acid esters, fatty acid alkanolamides and fatty acid glucamides, $C_8$-$C_{22}$ alkylmono- and oligoglycosides and their ethoxylated analogs, whereby oligomerization degrees of 1.1 to 5, in particular 1.2 to 2.0 and glucose as the sugar component are used, mixtures of alkyl(oligo)glucosides and fatty alcohols, e.g., the commercially available product Montanov® 68, addition products of 5 to 60 mol ethylene oxide onto castor oil and hardened castor oil, partial esters of polyols with 3 to 6 carbon atoms with saturated fatty acids with 8 to 22 carbon atoms, sterols; sterols are understood to be a group of steroids which have a hydroxyl group on carbon 3 of the steroid structure and are isolated from both animal tissue (zoosterols) and vegetable fats (phytosterols). Examples of zoosterols include cholesterol and lanosterol. Examples of suitable phytosterols include ergosterol, stigmasterol and sitosterol. Sterols and mycosterols are also isolated from fungi and yeasts.

phospholipids; these include especially the glucose phospholipids, which are obtained, e.g., as lecithins and/or phosphatidylcholines from egg yolk or plant seeds (e.g., soybeans), for example, fatty acid esters of sugars and sugar alcohols such as sorbitol, polyglycerols and polyglycerol derivatives such as polyglycerol, poly-12-hydroxystearat (commercially available as Dehymuls® PGPH), linear and branched fatty acids with 8 to 30 carbon atoms and their Na, K, ammonium, Ca, Mg and Zn salts.

The emulsifiers are used in amounts of 0.1 to 25 wt.-%, in particular 0.1 to 3 wt.-%, based on the respective total composition.

Another important group of fabric softener ingredients, detergent and cleaning agent ingredients is the builder substances. This substance class is understood to include both organic and inorganic builder substances. These are compounds that can have a carrier function in the compositions as well as acting as a water softener substance in use.

Suitable builders include, for example, alkali metal gluconates, citrates, nitrilotriacetate, carbonates and bicarbonates, in particular, sodium gluconate, citrate and nitrilotriacetate as well as sodium and potassium carbonate and bicarbonate and alkali metal hydroxides and alkaline earth metal hydroxides, in particular sodium and potassium hydroxide, ammonium and amines, in particular, mono- and triethanolamine and/or mixtures thereof. These also include the salts of glutaric acid, succinic acid, adipic acid, tartaric acid and benzenehexacarboxylic acid as well as phosphonates and phosphates.

Usable organic builder substances include, for example, the polycarboxylic acids that may be used in the form of their sodium salts, where polycarboxylic acids are understood to include those carboxylic acids having more than one acid function. For example, these include citric acid, adipic acid, succinic acid, glutaric acid, malic acid, tartaric acid, maleic acid, fumaric acid, sugar acids, aminocarboxylic acids, nitrilotriacetic acid (NTA), if such a use is not objectionable for ecological reasons, as well as mixtures thereof. Non-limiting salts include the salts of polycarboxylic acids such as citric acid, adipic acid, succinic acid, glutaric acid, tartaric acid, sugar acids and mixtures thereof. The acids per se may also be used. In addition to their builder effect, the acids typically also have the property of an acidifying component and thus also serve to adjust a lower and milder pH of detergents or cleaning agents, as in the inventive granules, for example. Citric acid, succinic acid, glutaric acid, adipic acid, gluconic acid and any mixtures thereof may be mentioned here, in particular.

Also polymeric polycarboxylates are suitable as builders, including the alkali metal salts of polyacrylic acid or polymethacrylic acid, e.g., those with a number average molecular weight of 500 g/mol to 70,000 g/mol. The (co)polymeric polycarboxylates may be used either as a powder or as an aqueous solution. The (co)polymeric polycarboxylate content of the compositions is 0.5 to 20 wt.-%, in particular, 3 to 10 wt.-%.

To improve the water solubility, the polymers may also contain allylsulfonic acid, allyloxybenzenesulfonic acid and methallylsulfonic acid as monomers. Biogradable polymers of more than two different monomer units, e.g., those containing as monomer salts of acrylic acid and maleic acid as well as vinyl alcohol and/or vinyl alcohol derivatives or containing as monomers salts of acrylic acid and 2-alkylallylsulfonic acid as well as sugar derivatives are used, in particular. Other copolymers include those having as monomers acrolein and acrylic acid/acrylic acid salts and/or acrolein and vinyl acetate. Likewise, polymeric aminodicarboxylic acids, their salts or their precursor substances are also to be mentioned as additional builder substances. Polyaspartic acids and/or their salts and derivatives which also have a bleach-stabilizing effect in addition to co-builder properties are used.

Other suitable builder substances include polyacetals, which may be obtained by reacting dialdehydes with polycarboxylic acids having 5 to 7 carbon atoms and at least three hydroxyl groups. Non-limiting polyacetals are obtained from dialdehydes such as glyoxal, glutaraldehyde, terephthalaldehyde and mixtures thereof and from polycarboxylic acids such as gluconic acid and/or glucoheptonic acid.

Other suitable organic builder substances include dextrins, e.g., oligomers and/or polymers of carbohydrates which can be obtained by partial hydrolysis of starches. The hydrolysis may be performed according to conventional methods, e.g., acid- or enzyme-catalyzed methods. These are hydrolysis products with number average molecular weights in the range of 400 to 500,000 g/mol. A polysaccharide with a dextrose equivalent (DE) in the range of 0.5 to 40, in particular, 2 to 30, is possible, where DE is a conventional measure of the reducing effect of a polysaccharide in comparison with dextrose, which has a DE of 100. Maltodextrins with a DE between 3 and 20 and dry glucose syrups with a DE between 20 and 30 as well as yellow dextrins and white dextrins with higher molecular weights in the range of 2,000 to 30,000 g/mol may be used. The oxidized derivatives of such dextrins are their reaction products with oxidizing agents which are capable of oxidizing at least one alcohol function of the saccharide ring to the carboxylic acid function.

Oxydisuccinates and other derivatives of disuccinates, such as ethylenediaminedisuccinate, are also suitable co-builders. Ethylenediamine-N,N'-disuccinate (EDDS) is used in the form of its sodium or magnesium salts. Also possible are glycerol disuccinates and glycerol trisuccinates. Suitable amounts for use in compositions containing zeolite and/or silicate are from 3 to 15 wt.-%.

Other organic co-builders that may also be used include, for example, acetylated hydroxycarboxylic acids and/or the salts thereof, which may also be in lactone form and which have at least four carbon atoms and at least one hydroxyl group plus max. two acid groups.

Another substance class with co-builder properties are the phosphonates. These are, in particular, hydroxyalkanephosphonates and/or aminoalkanephosphonates. Of the hydroxyalkanephosphonates, 1-hydroxyethane-1,1-diphosphonate (HEDP) is especially important as a co-builder. It is preferably used as a sodium salt, whereby the disodium salt gives a neutral reaction and the tetrasodium salt gives an alkaline reaction (pH 9). Non-limiting examples including ethylenediaminetetramethylenephosphonate (EDTMP), diethylenetriamine-pentamethylenephosphonate (DTPMP) and their higher homologs may be used as the aminoalkanephosphonates. They are used in the form of the neutral reacting sodium salts, e.g., as hexasodium salt of EDTMP and/or as hepta- and octasodium salts of DTPMP. From the class of phosphonates, HEDP is used as a builder.

The aminoalkanephosphonates also have a marked heavy metal binding capacity. Accordingly, in particular when the agents also contain bleaches, it may be possible to use aminoalkane-phosphonates, in particular, DTPMP, or mixtures of the aforementioned phosphonates.

In addition, all compounds capable of forming complexes with alkaline earth ions may also be used as co-builders.

A non-limiting inorganic builder is a finely crystalline synthetic zeolite containing bound water. The finely crystalline synthetic zeolite containing bound water used here is zeolite A and/or P. For example, zeolite MAP, e.g., Doucil A24® (commercially available from the company Crosfield) is used as zeolite P. However, zeolite X and mixtures of A, X and/or P, e.g., a co-crystal product of the zeolites A and X, Vegobond® AX (commercial available from Condea August S.p.A.) are also suitable. The zeolite may be used as a spray-dried powder or as an undried stabilized emulsion, which is still moist from its preparation. For the case when the zeolite is used as a suspension, it may contain small added amounts of nonionic surfactants as stabilizer, e.g., 1 to 3 wt.-% based on the weight of total zeolite, of ethoxylated $C_{12}$-$C_{18}$ fatty alcohols with two to five ethylene oxide groups, $C_{12}$-$C_{14}$ fatty alcohols with four to five ethylene oxide groups or ethoxylated isotridecanols. Suitable zeolites have an average particle size of less than 10 μM (volume distribution; measurement method: Coulter counter) and contain 18 to 22 wt.-%, in particular, 20 to 22 wt.-% bound water. In embodiments, zeolites are present in the premix in amounts of 10 to 94.5 wt.-%, but zeolites may be present in amounts of 20 to 70 wt.-%, in particular 30 to 60 wt.-% Suitable partial substitutes for zeolites include sheet silicates of natural and synthetic origin. Their usability is not limited to a specific composition and/or structural formula. However, smectites, in particular bentonites, are possible. Crystalline sheet sodium silicates of the general formula $NaMSi_xO_{2x+1}*yH_2O$, where M denotes sodium or hydrogen, x denotes a number from 1.9 to 4 and y denotes a number from 0 to 20, such as values for x are 2, 3 or 4 are suitable for substitution of zeolites or phosphates. Non-limiting crystalline sheet silicates of the given formula include those in which M stands for sodium and x assumes values of 2 or 3. In particular, both β- and δ-sodium disilicates $Na_2Si_2O_5 \cdot yH_2O$ are used.

It is also possible to use the generally known phosphates as builder substances if such a use should not be avoided for ecological reasons. In particular, the sodium salts of orthophosphates, pyrophosphates and, in particular, tripolyphosphates are suitable.

The agents contain builders in amounts, based on the total weight of the composition, of 0 to 20 wt.-% such as from 0.01 to 12 wt.-%, alternatively from 0.1 to 8 wt.-%, or from 0.3 to 5 wt.-%.

In addition to the ingredients already listed, the inventive detergents and cleaning agents may additionally contain one or more substances from the group of bleaching agents, bleach activators, enzymes, pH adjusting agents, fluorescent agents, dyes, foam inhibitors, silicone oils, anti-redeposition agents, optical brighteners, graying inhibitors, dye transfer inhibitors, corrosion inhibitors and silver protectants. These substances are described below.

Of the compounds that yield $H_2O_2$ in water and serve as bleaching agents, sodium perborate tetrahydrate, sodium perborate monohydrate and sodium percarbonate are used. Other bleaching agents that may be used include, for example, peroxypyrophosphates, citrate perhydrates and peracid salts or peracids that supply $H_2O_2$ such as perbenzoates, peroxophthalates, diperazelaic acid, phthaloimino peracid or diperdodecanedioic acid. When using bleaching agents, it is also possible to omit the use of surfactants and/or builders, so that pure bleaching agent tablets can be produced. If such bleaching agent tablets are to be used for washing laundry, then a combination of sodium percarbonate with sodium sesquicarbonate is possible, regardless of which additional ingredients are present in the molded bodies. If cleaning agents or bleaching agent tablets are produced for machine dishwashing, bleaching agents from the group of organic bleaching agents may also be used. Typical organic bleaching agents include the diacyl peroxides, e.g., dibenzoyl peroxide. Other typical organic bleaching agents include the peroxy acids, where the alkylperoxy acids and arylperoxy acids may be mentioned, in particular, as examples. Non-limiting representatives include (a) peroxybenzoic acid and its ring-substituted derivatives, such as alkylperoxybenzoic acids as well as peroxy-α-naphthoic acid and magnesium monoperphthalate, (b) the aliphatic or substituted aliphatic peroxy acids such as peroxylauric acid, peroxystearic acid, ε-phthalimidoperoxycaproic acid (phthaloiminoperoxyhexanoic acid (PAP)), o-carboxybenzamidoperoxycaproic acid, N-nonenylamidoperadipic acid and N-nonenylamidopersuccinates and (c) aliphatic and aralipathic peroxydicarboxylic acids such as 1,12-diperoxyphthalic acid, 1,9-diperoxyazelaic acid, diperoxysebacic acid, diperoxybrassylic acid, diperoxyphthalic acids, 2-decyldiperoxybutane-1,4-diacid, N,N-terephthaloyldi-(6-aminopercaproic acid) may also be used.

Substances that release chlorine or bromine may also be used as bleaching agents in agents for machine dishwashing. Of the suitable materials that release chlorine or bromine, heterocyclic N-bromo and N-chloroamides may be considered, e.g., trichloroisocyanuric acid, tribromoisocyanuric acid, dibromoisocyanuric acid and/or dichloroisocyanuric acid (DICA) and/or the salts thereof with cations such as potassium and sodium. Hydantoin compounds such as 1,3-dichloro-5,5-dimethylhydantoin are also suitable.

To achieve an improved bleaching effect when washing or cleaning at temperatures of 60° C. or lower, bleach activators may also be incorporated into the inventive detergents and cleaning agents. Bleach activators may include compounds that yield aliphatic peroxocarboxylic acids with 1 to 10 carbon atoms, such as 2 to 4 carbon atoms and/or optionally substituted perbenzoic acid under perhydrolysis conditions may be used as bleach activators. Substances that have O-acyl groups and/or N-acyl groups with the aforementioned number of carbon atoms and/or optionally substituted benzoyl groups are suitable. Polyacylated alkylenediamines, in particular, tetraacetylethylenediamine (TAED), acylated triazine derivatives, in particular, 1,5-diacetyl-2,4-dioxohexahydro-1,3,5-triazine (DAD HT), acylated glycolurils, in particular, tetraacetylglycoluril (TAGU), N-acylimide, in particular, N-nonanoylsuccinimide (NOSI), acylated phenolsulfonates, in particular, n-nonanoyl- or isononanoyloxybenzene sulfonate (n- and/or iso-NOBS), carboxylic anhydride, in particular, phthalic anhydride, acylated polyvalent alcohols, in particular, triacetin, ethylene glycol diacetate and 2,5-diacetoxy-2,5-dihydrofuran are used.

In addition to or in place of the conventional bleach activators, bleach catalysts may also be present. These substances are bleach-potentiating transition metal salts and/or transition metal complexes, e.g., Mn, Fe, Co, Ru or Mo saline complexes or carbonyl complexes. Mn, Fe, Co, Ru, Mo, Ti, V and Cu complexes with tripod ligands containing N as well as Co, Fe, Cu and Ru-ammine complexes may also be used as bleach catalysts.

The enzymes that may be used include those from the class of proteases, lipases, amylases, cellulases and/or mixtures thereof. Enzymatic active ingredients obtained from bacterial strains or fungi, e.g., *Bacillus subtilis, Bacillus licheniformis* and *Streptomyces griseus* are especially suitable. Proteases of the subtilisin type and, in particular, proteases obtained from *Bacillus lentus* are used. Enzyme mixtures, e.g., from protease and amylase or protease and lipase or protease and lipase or protease and cellulase or from cellulase and lipase or from protease, amylase and lipase or protease, lipase and cellulase, but in particular mixtures containing cellulase are of special interest. Peroxidases or oxidases have also proven suitable in some cases. The enzymes may be adsorbed onto carrier substances and/or embedded in sheathing substances to protect them from premature decomposition. The amount of enzymes, enzyme mixtures or enzyme granules in the inventive molded bodies may be 0.1 to 5 wt.-%, such as 0.1 to approx. 2 wt.-%, based on the total weight of the composition. The most commonly used enzymes include lipases, amylases, cellulases and proteases. Non-limiting proteases include BLAP® 140 from the company Biozym, Optimase® M-440 and Opticlean® M-250 from the company Solvay Enzymes; Maxacal® CX and Maxapem® or Esperase® from the company Gist Brocades or Savinase® from the company Novo. Especially suitable cellulases and lipases include Celluzym® 0.7 T and Lipolase® 30 T from the company Novo Nordisk. Duramyl® and Termamyl® 60 T and Termamyl® 90 T from the company Novo, Amylase-LT® from the company Solvay Enzymes or Maxamyl® P5000 from the company Gist Brocades are used, in particular. Other enzymes may also be used.

In addition, the detergents and cleaning agents may also contain components which have a positive influence on the release of oil and fat from textiles (soil repellents). This effect becomes especially pronounced when a textile that has already been washed repeatedly with an inventive detergent containing this oil- and fat-releasing component is soiled. The oil- and fat-releasing components include, for example, nonionic cellulose ethers such as methyl cellulose and methyl hydroxypropyl cellulose with a methoxyl group content of 15 to 30 wt.-% and a hydroxypropoxyl group content of 1 to 15 wt.-%, each based on the nonionic cellulose ether, as well as the polymers of phthalic acid and/or terephthalic acid known from the state of the art and/or their derivatives, in particular, polymers of ethylene terephthalates and polyethylene glycol terephthalates or anionically and/or nonionically modified derivatives thereof. Of these, the sulfonated derivatives of phthalic acid polymers and terephthalic acid polymers are especially used.

In addition, the agents may also contain as optical brighteners derivatives of diaminestilbenedisulfonic acid and/or its alkali metal salts. For example, the salts of 4,4'-bis(2-anilino-4-morpholino-1,3,5-triazinyl-6-amino)stilbene-2,2'-disulfonic acid or similarly constructed compounds which have a diethanolamino group, a methylamino group, an anilino group or a 2-methoxyethylamino group instead of the morpholino group are also suitable. In addition, brighteners of the substituted diphenylstyryl type may also be present, e.g., the alkali salts of 4,4'-bis(2-sulfostyryl)diphenyl, 4,4'-bis(4-chloro-3-sulfostyryl)diphenyl or 4-(4-chlorostyryl)-4'-(2-sulfostyryl)diphenyl. Mixtures of the aforementioned brighteners may also be used.

To improve the aesthetic impression of the inventive agents, they may be pigmented with suitable dyes. Non-limiting dyes, the selection of which will not pose any problems for those skilled in the art, have a high stability in storage and are insensitive to the other ingredients of the agents and to light, and do not have any pronounced substantivity with respect to textile fibers, so as not to stain the latter.

According to a non-limiting embodiment, detergents and cleaning agents also include dishwashing agents. The inventive dishwashing agents may contain corrosion inhibitors to protect the washed utensils or the machine, whereby, in particular, silver protectants have a special importance in the field of machine dishwashing. In general, silver protectants selected from the group of triazoles, benzotriazoles, bisbenzotriazoles, aminotriazoles, alkylaminotriazoles and transition metal salts or complexes may be used, in particular. Benzotriazole and/or alkylaminotriazole are especially for use. In addition, cleaning agent formulations frequently also contain agents having active chlorine which can significantly reduce corrosion on the surface of silver. In chlorine-free cleaners, oxygen-containing and nitrogen-containing organic redox-active compounds are used in particular, such as divalent and trivalent phenols, e.g., hydroquinone, pyrocatechol, hydroxyhydroquinone, gallic acid, phloroglucine, pyrogallol and/or derivatives of these classes of compounds. Salt-like and complex-like inorganic compounds, e.g., the salts of the metals Mn, Ti, Zr, Hf, V, Co and Ce are frequently also used. Transition metal salts selected from the group of manganese and/or cobalt salts and/or complexes are possible, such as the cobalt-(ammine) complexes, the cobalt-(acetate) complexes, the cobalt-(carbonyl) complexes, the chlorides of cobalt or manganese and of manganese sulfate. Likewise, zinc compounds may be used to prevent corrosion of the washed utensils.

Special ingredients that may be used in the inventive agents for machine dishwashing or for cleaning hard surfaces include substances to prevent re-soiling of surfaces and/or to facilitate the release of dirt after a single use ("soil-release compounds").

The soil-release compounds that may be used include all those compounds known in the state of the art. Especially suitable examples include cationic polymers, e.g., hydroxypropyltrimethylammonium guar, copolymers of aminoethyl methacrylate and acrylamide as well as copolymers of dimethyldiallylammonium chloride and acrylamide, polymers with imino groups, cationic cellulose derivatives, cationic homopolymers and/or copolymers (monomer units: quaternated ammonium alkyl methacrylate groups).

The cationic polymers are selected from cationic polymers of copolymers of monomers such as trialkylammonium alkyl (meth)acrylate and/or acrylamide; dialkyldiallyldiammonium salts; polymer-like reaction products of ethers or esters of polysaccharides with ammonium side groups, in particular, guar derivatives, cellulose derivatives and starch derivatives; polyadducts of ethylene oxide with ammonium groups; quaternary ethyleneimine polymers and polyesters and polyamides with quaternary side groups as soil-release compounds. Natural polyuronic acids and related substances as well as polyampholytes and hydrophobized polyampholytes and/or mixtures of these substances are also used.

This list of ingredients of fabric softeners and detergents and cleaning agents is by no means comprehensive but instead merely gives the most essential typical ingredients of such agents. In particular, inasmuch as they are liquid or gel preparations, these agents may also contain organic solvents. These are monovalent or polyvalent alcohols with 1 to 4 carbon atoms. Non-limiting alcohols in such agents include ethanol, 1,2-propanediol, glycerol as well as mixtures of these alcohols. In non-limiting embodiments, such agents contain 2 to 12 wt.-% of such alcohols, based on the total weight of the composition.

Essentially the agents may have different physical states. In another embodiment, the fabric softeners, detergents or cleaning agents are liquid or gel agents, in particular, liquid detergents or liquid dishwashing detergents or cleaning gels, and they may, in particular, also be cleaning agents in the form of gels for cleaning toilets.

These are intrinsically viscous cleaning agents in the form of gels with a viscosity of 30,000 to 150,000 mPas, containing as the gelatinizing agent a polysaccharide or a fatty alcohol alkoxylate as described above, as the optional emulsifier and wetting-active component a $C_{8-10}$ alkyl polyglycoside or $C_{12-14}$ alkyl polyglycoside and perfume oil. Fatty alcohol ether sulfates (FAEOS) and fatty alcohol sulfates (FAS) may also be present as additional co-surfactants. The ratio of APG to co-surfactant is then usually greater than 1, such as between 50:1 and 1:1, alternatively between 10:1 and 1.5 to 1 or between 5:1 and 1.8:1. In particular these are stable, shear-diluting cleaning agents in the form of a gel containing a polysaccharide, a surfactant system and perfume components. Alternatively, they can contain a polysaccharide, such as a xanthan gum, in amounts between 1 and 5 wt.-%, such as from 1 to 5 wt.-%, alternatively from 1.5 to 3.5 wt.-% or from 1.8 to 3 wt.-% optionally they contain as a component of the surfactant system a $C_{8-22}$ alkyl polyglycoside in amounts between 3 and 25 wt.-%, such as from 4 and 20 wt.-%, alternatively from 5 and 15 wt.-% or from 5 and 12 wt.-% and they contain the perfume component(s) up to 15 wt.-%, such as from 2 to 12 wt.-%, alternatively from 3 to 8 wt.-%, and they optionally contain other ingredients such as lime-dissolving agents, dyes, microbicidal agents (e.g., isothiazoline mixtures, sodium benzoate or salicylic acid), pearlescent agents, stabilizers, cleaning enhancers and odor absorbers, and the agents have a viscosity of 30,000 to 150,000 mPas, measured with a Brookfield rotary viscometer, model RVT with a Helipath device and TA spindle at 1 rpm and 23° C.

If necessary, water-soluble and water-insoluble builders may also be present in gels. Water-soluble builders are then used because they usually have less tendency to form insoluble residues on hard surfaces. The usual builders which may be present include the low-molecular polycarboxylic acids and their salts, the homopolymeric and copolymeric polycarboxylic acids and their salts, citric acid and its salts, carbonates, phosphates and silicates. The water-insoluble builders include the zeolite, which may also be used as well as the mixtures of the aforementioned builder substances. The group of citrates is especially possible. Other typical cleaning agents which may contain the inventive compounds or mixtures include liquid or gel cleaners for hard surfaces, in particular, all-purpose cleaners, glass cleaners, floor and bathroom cleaners as well as special embodiments of such cleaners, which include acidic or alkaline forms of all-purpose cleaners as well as glass cleaners with an anti-rain effect. These liquid cleaning agents may also be present in one or more phases. In an embodiment, the cleaners have two different phases.

"Cleaner" in the broadest sense is a term for formulations (e.g. containing a surfactant) with a very wide area of application and a very different composition, depending on the application. The most important market segments are household cleaners, industrial (technical) cleaners and institutional cleaners. Depending on the pH, a distinction is made between alkaline, neutral and acidic cleaners; according to the form in which it is offered, a distinction is made between liquid and solid cleaners (also in tablet form). These cleaners for hard surfaces yield an optimal profile of use (in contrast with dishwashing agents, which are also classified in the product group of cleaners) both in a concentrated state and in dilute aqueous solution when combined with mechanical energy. Low-temperature cleaners manifest their effect without elevated temperature. Surfactants and/or alkali carriers, alternatively acids, optionally also solvents such as glycol ethers and lower alcohols can provide for the cleaning effect. In general, the formulations also contain builders and, depending on the type of cleaner, bleaching agents, enzymes, microbicidal or disinfecting additives as well as perfume oils and dyes. Cleaners may also be formulated as microemulsions. The success of cleaning depends to a great extent on the type of dirt-which may also vary greatly geographically- and the properties of the surfaces to be cleaned.

Household cleaners may be formulated as universal cleaners or as special cleaners for ceramics, tiles, windows, plastics, (carpet) floors, cook-tops, baking ovens, microwave ovens, plumbing cleaners or bathroom or toilet cleaners. Pipe cleaners are adjusted to be alkaline and consist of, for example, solid sodium hydroxide and aluminum powder which, when dissolved, release hydrogen, which ensures a corresponding turbulence in the pipe segments to be cleared. In addition to containing surfactant and builder, sanitary cleaners mainly contain active ingredients to reduce the microbe count, whereby sodium hypochlorite, which was used previously, has been partially replaced by hydrogen peroxide or other peracid compounds. Toilet cleaners are mainly acidic but may sometimes also be adjusted to be alkaline, whereby in the former case, the phosphoric acid originally used and sodium bisulfate are largely replaced by organic acids, mainly citric acid. Special cleaners also include automotive cleaners, automobile windshield cleaners, wheel rim cleaners, engine cleaners and paint application equipment cleaners in the do-it-yourself area.

In addition to the components already mentioned, the inventive agents may also contain other additives and aids, such as those customary in such agents. These include, in particular, polymers, soil-release active ingredients, solvents (e.g., ethanol, isopropanol, glycol ether), solubilizers, hydrotropes (e.g., cumenesulfonate, octyl sulfate, butyl glucoside, butyl glycol), cleaning enhancers, viscosity regulators (e.g., synthetic polymers, such as polysaccharides, polyacrylates, naturally occurring polymers and their derivatives such as xanthan gum, other polysaccharides and/or gelatins), pH regulators (e.g., citric acid, alkanolamines or NaOH), disinfectants, antistatics, preservatives, bleach systems, enzymes, dyes and opacifiers or skin protectants.

The amount of such additives is usually no more than 12 wt.-% in the compositions. The lower limit depends on the type of additive and may be up to 0.001 wt.-% or less in the case of dyes. The amount of auxiliaries is between 0.01 and 7 wt.-%, in particular, 0.1 and 4 wt.-%.

The aforementioned agents may also contain binders, which may be used alone or in mixture with other binders. Non-limiting binders include polyethylene glycols, 1,2-polypropylene glycols and modified polyethylene glycols and polypropylene glycols. The modified polyalkylene glycols include, in particular, the sulfates and/or disulfates of polyethylene glycols or polypropylene glycols with a relative molecular weight between 600 and 12,000 g/mol and, in particular, between 1,000 and 4,000 g/mol. Another group consists of monosuccinates and/or disuccinates of polyalkylene glycols, which in turn have relative molecular weights between 600 and 6,000 g/mol, such as between 1,000 and 4,000 g/mol.

and 6,000 g/mol, such as between 1,000 and 4,000 g/mol.

Within the present embodiments, polyethylene glycols include polymers for whose production $C_3$-$C_5$ glycols as well as glycerol and mixtures of these are used as initiator molecules in addition to ethylene glycol. Furthermore, ethoxylated derivatives such as trimethylolpropane with 5 to 30 ethylene oxides (EO) are also included. The polyethylene glycols that are for use may have a linear or branched structure, but linear polyethylene glycols are particularly possible. The polyethylene glycols include, in particular, those with relative molecular weights between 2,000 and 12,000 g/mol, advantageously 4,000 g/mol, whereby polyethylene glycols with number average molecular weights of less than 3,500 g/mol and greater than 5,000 g/mol may be used, in particular, in combination with polyethylene glycols with a relative molecular weight of 4,000 g/mol, and such combinations advantageously have more than 50 wt.-%, based on the total amount of polyethylene glycols, polyethylene glycols with a relative molecular weight between 3,500 and 5,000 g/mol. However, polyethylene glycols which are in a liquid state at room temperature and a pressure of 1 bar may also be used as binders; this refers mainly to polyethylene glycol with a relative molecular weight of 200, 400 and 600. However, these essentially liquid polyethylene glycols should be used only in a mixture with at least one other binder, whereby this mixture must again meet the inventive requirements, i.e., must have a melting point and/or a softening point at least higher than 45° C.

Low-molecular polyvinylpyrrolidones and derivatives of these with relative molecular weights up to max. 30,000 are also suitable as binders. Relative molecular weight ranges between 3,000 and 30,000 are possible, e.g., 10,000. Polyvinylpyrrolidones are not used as exclusive binders but instead are used in combination with others, in particular, in combination with polyethylene glycols.

Other suitable binders have proven to be raw materials, said raw materials having detergent-active or cleaning-active properties, i.e., for example, nonionic surfactants with a melting point of at least 45° C. or mixtures of nonionic surfactants and other binders. The nonionic surfactants include alkoxylated fatty alcohols or oxo alcohols, in particular, $C_{12-18}$ alcohols. Degrees of alkoxylation, in particular, degrees of ethoxylation, of 8 to 80 AO on the average, in particular, ethylene oxide (EO) per mol alcohol and mixtures of these have proven to be especially suitable. Especially fatty alcohols with an average of 12 to 35 EO, in particular, with an average of 20 to 25 EO have advantageous binder properties. If necessary, ethoxylated alcohols with an average of a few EO units per mol alcohol may also be present in binder mixtures, e.g., tallow fatty alcohol with 14 EO. However, it is possible to use these relatively low ethoxylated alcohols only in mixture with higher ethoxylated alcohols. The content of these relatively low ethoxylated alcohols in the binder, advantageously, amounts to less than 50 wt.-%, in particular, less than 40.-wt.-%, based on the total amount of binder. Nonionic surfactants that are generally used, especially in detergents or cleaning agents, such as $C_{12-18}$ alcohols with an average of 3 to 7 EO, which are liquid at room temperature, are present in the binder mixtures only in amounts of less than 2 wt.-%.

It is likewise possible for conventional anionic surfactants that are used in detergents or cleaning agents or their precursors, the anionic surfactant acids, to be present in the binder mixture. Other nonionic surfactants that are suitable as binders include the fatty acid methyl ester ethoxylates, which do not tend to gel, in particular those with an average of 10 to 25 EO (for a more detailed description of this substance group, see below). Representatives of this substance group include primarily the methyl esters based on $C_{16-18}$ fatty acids, e.g., hardened bovine tallow methyl esters with an average of 12 EO or with an average of 20 Ea In a non-limiting embodiment, a mixture containing $C_{12-18}$ fatty alcohol, based on coconut or tallow with an average of 20 EO, and polyethylene glycol with a relative molecular weight of 400 to 4,000 g/mol is used as the binder. In another embodiment, a mixture containing mainly methyl esters based primarily on $C_{16-18}$ fatty acids and with an average of 10 to 25 EO, in particular, hardened bovine tallow methyl esters with an average of 12 EO or an average of 20 EO, and a $C_{12-18}$ fatty alcohol based on coconut or tallow with an average of 20 EO and/or polyethylene glycol with a relative molecular weight of 400 to 4,000 g/mol, is used as the binder.

Binders based either only on polyethylene glycols with a relative molecular weight of 4,000 or on a mixture of $C_{12-18}$ fatty alcohol based on coconut or tallow with an average of 20 EO and one of the fatty acid methyl ester ethoxylates described above or on a mixture of $C_{12-18}$ fatty alcohol based on coconut or tallow with an average of 20 EO, one of the fatty acid methyl ester ethoxylates described above and a polyethylene glycol, in particular, with a relative molecular weight of 4,000 g/mol, have proven to be especially advantageous embodiments.

The inventive agents may contain, e.g., carbonate/citric acid systems as suitable and well-known disintegration aids, but other organic acids may also be used. Swelling disintegration aids include, for example, synthetic polymers such as polyvinylpyrrolidone (PVP) or natural polymers and/or modified natural substances such as cellulose and starch and their derivatives, alginate or casein derivatives.

Disintegrants based on cellulose are used as the disintegrants, so that molded bodies of detergent and cleaning agent will contain such a disintegrant based on cellulose in amounts of 0.5 to 10 wt.-%, such as 3 to 7 wt.-% and in particular 4 to 6 wt.-%. Pure cellulose has the formal empirical composition ($C_6H_{10}O_5$) and, considered formally, is a β-1,4-polyacetal of cellobiose, which in turn is made up of two molecules of glucose. Suitable celluloses consist of approx. 500 to 5,000 glucose units and consequently have a number average molecular weight of 50,000 to 500,000 g/mol. Cellulose derivatives, which are also available from cellulose by polymer-like reactions, may be used as disintegrants based on cellulose. Such chemically modified celluloses comprise, for example, products of esterifications and/or etherifications in which hydroxyhydrogen atoms have been substituted. However, celluloses in which the hydroxyl groups have been replaced by functional groups that are not bound by an oxygen atom may also be used as cellulose derivatives. The group of cellulose derivatives includes, for example, alkali celluloses, carboxymethylcellulose (CMC), cellulose esters and ethers as well as aminocelluloses. The aforementioned cellulose derivatives are not used alone as disintegrants based on cellulose but instead are used in mixture with cellulose. The cellulose derivative content of these mixtures is less than 50 wt.-%, such as less than 20 wt.-%, based on the disintegrant based on cellulose. Pure cellulose free of cellulose derivatives is especially used as the disintegrant based on cellulose.

The cellulose that is used as the disintegration aid is not used in finely divided form but instead is converted to a coarser form, e.g., granular or compacted, before being added to the premixes to be pressed.

The particle size of such disintegrants is usually greater than 200 μm, such as at least 90 wt.-% being between 300 and 1,600 μm, and in particular at least 90 wt.-% being between 400 and 1,200 μm.

Microcrystalline cellulose may be used as another disintegrant based on cellulose or as an ingredient of these components. This microcrystalline cellulose is obtained by partial hydrolysis of celluloses under such conditions that attack only the amorphous regions (approx. 30% of the total cellulose mass) of the celluloses and completely dissolve them, but leave the crystalline regions (approx. 70%) undamaged. Subsequent deaggregation of the microfine celluloses obtained by hydrolysis yields microcrystalline celluloses, which have primary particle sizes of approx. 5 μm and can be compacted to granules with an average particle size of 200 μm, for example.

In a variant, the detergents and cleaning agents, in particular, in the form of molded bodies such as tablets, contain 0.5 to 10 wt.-%, such as 3 to 7 wt.-% and, in particular, 4 to 6 wt.-% of one or more disintegration aids, each based on the weight of the molded body.

Another subject matter is cosmetics (cosmetic agents) for cosmetic, non-therapeutic treatment of hair or skin, containing the inventive compounds or mixtures. These cosmetic (cosmetic agents) contain the inventive compounds or mixtures in amounts of 0.001 to 10 wt.-%, such as from 0.01 to 5 wt.-%, alternatively 0.02 to 3 wt.-% or in amounts of 0.05 to 2 wt.-%, each based on the total weight of the composition.

The total amount of scent substances in the cosmetic agents, however, is between 0.01 and 5 wt.-%, such as between 0.1 and 3 wt.-% or between 0.5 and 2 wt.-%, based on the total amount of the agent. Mixtures of various scent substances (from the various classes of scent substances mentioned above) which jointly produce an appealing scent note are used.

In an embodiment, the cosmetic agents are aqueous preparations that contain surfactant active ingredients and are suitable, in particular, for treatment of keratin fibers, in particular human hair, or for cosmetic (non-therapeutic) treatment of skin.

The hair treatment agents mentioned above include, in particular, agents for treatment of human head hair. The most conventional agents of this category can be divided into shampoo detergents, hair care agents, hair setting and permanent hair waving agents as well as hair dyes and depilatories. The agents may contain surfactant active ingredients and are in particular shampoos and treatment preparations. Such a hair washing agent or shampoo consist of 10 to 20 recipe ingredients, in individual cases up to 30 recipe ingredients. These aqueous preparations are usually in liquid form to pasty form.

The inventive cosmetics (cosmetic agents) contain other ingredients that are conventional for these agents. The inventive cosmetic agents contain surfactant active ingredients or detergent-active ingredients as additional ingredients. Fatty alcohol polyglycol ether sulfates (ether sulfates, alkyl ether sulfates) are used here, partially in combination with other surfactants, usually anionics. In addition to the alkyl ether sulfates, agents may additionally contain other surfactants such as alkyl sulfates, alkyl ether carboxylates, such as with degrees of ethoxylation of 4 to 10, as well as surfactant protein-fatty acid condensates. Protein-abitic acid condensate in particular should be mentioned. Sulfosuccinic acid esters, amidopropyl-betaines, amphoacetates and amphodiacetates as well as alkyl polyglycosides are surfactants that are used in shampoos.

Another group of ingredients is summarized by the term auxiliary substances and is extremely varied: for example, nonionic surfactant additives such as ethoxylated sorbitan esters or protein hydrolysates increase the compatibility and/or have an irritation-reducing effect, e.g., in baby shampoo; e.g., natural oils or synthetic fatty acid esters serve as moisturizing agents to prevent excessive removal of oil in shampooing; humectants include glycerol, sorbitol, propylene glycol (see propanediols), polyethylene glycols and other polyols. To improve wet combability and to reduce electrostatic charge buildup on the hair after drying, cationic surfactants, e.g., quaternary ammonium compounds, may be added to the shampoo. For a brilliant color appearance, dyes and/or pearlescent pigments may be added. To adjust the desired viscosity, thickeners of various substance classes may be used, and pH stability is achieved by buffers based on citrate, lactate or phosphate, for example. To ensure adequate stability and storage life, preservatives such as 4-hydroxybenzoic acid ester may be added; oxidation-sensitive ingredients can be protected by adding antioxidants such as ascorbic acid, butylmethoxyphenol or tocopherol.

Another group of ingredients include special active ingredients for special shampoos, e.g., oils, herbal extracts, proteins, vitamins and lecithins in shampoos for hair that becomes oily rapidly, for especially dry hair, stressed or damaged hair. Active ingredients in shampoos for controlling dandruff usually have a broad growth-inhibiting effect against fungi and bacteria. The fungistatic properties of pyrithione salts, in particular, have been shown to be the cause of the good antidandruff effect. To achieve a pleasant scent note, the shampoos can contain perfume oils. All conventional scent substances allowed for use in shampoo may also be used.

Hair care agents have the goal of preserving the natural condition of freshly washed hair as long as possible and restoring it if there is damage. Features characterizing this natural condition include a silky sheen, low porosity, a resilient and yet soft fullness and a pleasant smooth feel. An important prerequisite for this is a clean scalp, free of dandruff and without excessive oiliness. The hair care agents today include a variety of different products, the most important representatives of which are known as pretreatment agents, hair water, styling aids, hair rinses and hair repair kits and whose composition, like that of the shampoos, is broken down roughly into basic substances, auxiliary substances and special active ingredients.

The basic substances include fatty alcohols, especially cetyl alcohol (1-hexadecanol) and stearyl alcohol (1-octadecanol), waxes such as beeswax, wool wax (lanolin), synthetic waxes, paraffins, petrolatum, paraffin oil and as solvents mainly ethanol, 2-propanol and water. Additives include emulsifiers, thickeners, preservatives, antioxidants, coloring agents and perfume oils. The most important group of special active ingredients in hair care agents today are the quaternary ammonium compounds. A distinction is made between monomeric (e.g., alkyltrimethylammonium halide with mainly the lauryl, cetyl or stearyl group as the alkyl radical) and polymeric quaternary ammonium compounds (e.g., quaternary cellulose ether derivatives or poly(N,N-dimethyl-3,4-methylenepyrrolidinium chloride)). Their effect in hair care agents is based on the fact that the positive charge of the nitrogen atoms of this compound can be added to the negative charges of the keratin of hair; damaged hair contains more negatively charged acid groups because of its higher cysteic acid content and may therefore take up more quaternary ammonium compounds. Because of their cationic character, these compounds are also referred to as "cationic treatment substances" which have a smoothing effect on hair, improve combability, reduce electrostatic charge buildup, and improve the feel and sheen. The polymeric quaternary ammonium compounds adhere to hair so well that their effect can be detected even after several washings. Organic acids such as citric acid, tartaric acid or lactic acid are often used to adjust an acid medium. The water-soluble protein hydrolysates are absorbed well by the keratin of hair because of their close chemical relationship.

The largest group of special active ingredients in hair care agents comprise various plant extracts and plant oils.

These extracts are usually produced by extraction of the entire plant. However, in individual cases it may also be possible to prepare the extracts exclusively from the flowers and/or leaves of the plant.

With regard to the plant extracts, reference is made in particular to the extracts listed in the table beginning on page 44 of the third edition of Leitfaden zur Inhaltsstoffdeklaration kosmetischer Mittel [Guideline for Declaration of Ingredients of Cosmetic Agents], published by the Industrial Association of Body Care and Detergents (IKW), Frankfurt.

According to non-limiting embodiments, the extracts include especially those from green tea, oak bark, stinging nettle, witch hazel, hops, henna, chamomile, burdock root, horsetail, hawthorn, linden blossoms, almond, aloe vera, spruce needle, horse chestnut, sandalwood, juniper berry, coconut, mango, apricot, lemon, wheat, kiwi, melon, orange, grapefruit, sage, rosemary, birch, mallow, lady's smock, wild thyme, yarrow, thyme, lemon balm, restharrow, coltsfoot, marshmallow, meristem, ginseng and ginger root. Extracts of green tea, oak bark, stinging nettle, witch hazel, hops, chamomile, burdock root, horsetail, linden blossom, almond, aloe vera, coconut, mango, apricot, lemon, wheat, kiwi, melon, orange, grapefruit, sage, rosemary, birch, lady's smock, wild thyme, yarrow, restharrow, ginseng and ginger root are usable.

As extraction agents for producing the aforementioned plant extracts, water, alcohols and mixtures thereof may be used. Of the alcohols, low alcohols such as ethanol and isopropanol are used, but in particular, polyvalent alcohols such as ethylene glycol and propylene glycol are preferred as the sole extraction agent as well as in mixture with water. Plant extracts based on water/propylene glycol in a ratio of 1:10 to 10:1 have proven to be especially suitable.

The plant extracts may be used in both pure and diluted form. If they are used in diluted form, they usually contain approx. 2 to 80 wt.-% active substance and as a solvent the extraction agent or extraction agent mixture used in extracting them.

In addition, it may be possible to use mixtures of several plant extracts, in particular, to different plant extracts in the inventive agents.

To avoid moisturizing too rapidly, some hair waters contain substances such as certain tar ingredients, cysteic acid derivatives or glycyrrhizin; the intended reduction in sebaceous gland production has also not been proven conclusively. However, the efficacy of antidandruff agents has been satisfactorily proven. They are therefore used in the corresponding hair waters and similar hair care agents.

The aqueous preparations for treatment of skin include, in particular, preparations for care of human skin. This treatment begins with cleaning for the soaps which are used primarily. A distinction is made here between solid soap, usually in pieces, and liquid soap. Accordingly, the cosmetic agents in a non-limiting embodiment are in the form of molded bodies containing surfactant ingredients. In a non-limiting embodiment, the most important ingredients of such molded bodies are the alkali salts of the fatty acids of natural oils and fats, such as with chains of 12-18 carbon atoms. Since lauric acid soaps form suds especially well, the lauric acid-rich coconut and palm kernel oils are raw materials for production of fine soaps. The sodium salts of fatty acid mixture are solid, whereas the potassium salts are soft and pasty. For saponification, the dilute sodium hydroxide or potassium hydroxide solution is added to the fat raw materials in a stoichiometric ratio, so that the finished soap contains a lye excess of max. 0.05%. In many cases, soaps today are no longer prepared directly from fats but instead are prepared from the fatty acids obtained by splitting off fat. The usual soap additives include fatty acids, fatty alcohols, lanolin, lecithin, vegetable oils, partial glycerides and similar fat-like substances for moisturizing cleaned skin, antioxidants such as ascorbyl palmitate or tocopherol to prevent autoxidation of soap (rancidity), complexing agents such as nitrilotriacetate to bind traces of heavy metals which could act as catalysts in autoxidative spoilage, perfume oils to achieve the desired scent notes, coloring agents to color the pieces of soap and special additives, if necessary.

Liquid soaps are based on potassium salts of natural fatty acids as well as on synthetic anionic surfactants. They contain fewer detergent-active substances in aqueous solution than do solid soaps and have the usual additives, if necessary with viscosity-regulating components such as pearlescent additives. Because of their convenient and hygienic use from dispensers, they are used in public restrooms and the like. Washing lotions for especially sensitive skin are based on mild synthetic surfactants with additives of skin care substances, adjusted to a neutral pH or weakly acidic (pH 5.5).

There are a number of other preparations for cleaning and care of mainly the skin of the face such as face lotion, cleaning lotions, milks, creams, pastes; face packs are used for cleaning but primarily for refreshing and care of facial skin. Face lotions are usually aqueous alcoholic solutions with small amounts of surfactant and other skin care substances. Cleaning lotions, milk, creams and pastes are usually based on O/W emulsions with a relatively low amount of fat components with cleaning and care additives. Scruffing and peeling preparations contain mild keratolytic substances for removing the top horny layers of dead skin, in part with abrasive powder as additives.

Agents for cleaning treatment of uncleaned skin also further contain antibacterial and anti-inflammatory substances because the accumulations of sebum in comedones (pimples) constitute a culture medium for bacterial infections and tend to lead to inflammation. The broad range of different skin cleaning products that are available varies in composition and content of various active ingredients, coordinated with the various types of skin and for special treatment goals.

The bath additives offered for cleaning skin, in the bathtub or shower have been widely used. Bath salts and bath tablets should soften, color and perfume the bath water and usually do not contain any detergent-active substances. By softening the bath water, they promote the cleaning power of soaps but should primarily have a refreshing effect and enhance the bath experience. Bubble baths have a greater importance. With a larger amount of moisturizing and skin care substances, we also speak of cream baths.

The inventive cosmetics (cosmetic agents) may be present in different preparation forms. The most important are skin creams, skin lotions, skin oils and skin gels. The creams and lotions are based on emulsions in O/W (oil-in-water) form or W/O (water-in-oil) form. The main ingredients of the oil and/or fat or lipid phase preferably include fatty alcohols, fatty acids, fatty acid esters, waxes, petrolatum, paraffins and other fat and oil components mainly of a natural origin. In addition to water, the aqueous phase contains moisture-regulating and moisture-preserving substances as the main skin care active ingredients plus agents to regulate consistency and/or viscosity. Additional additives such as preservatives, antioxidants, complexing agents, perfume oils, coloring agents as well as special active ingredients are added to one of the aforementioned phases, depending on their solubility and stability properties. The choice of the emulsifier system is essential for the emulsion type and its properties. It can be selected according to the HLB system.

In addition, the skin care agents may contain other special active ingredients, e.g., milk protein products, egg yolk, lecithins, lipoids, phosphatides, cereal seed oils, vitamins, especially vitamin F and biotin, which was previously referred to as the skin vitamin (vitamin H) as well as hormone-free placenta extracts.

Skin oils are some of the oldest forms of skin care products and are still in use today. They are based on nondrying vegetable oils such as almond oil or olive oil with additives of natural vitamin oils such as wheat germ oil or avocado oil and oil-based plant extracts from St. John's wort, chamomile, etc.

Skin gels are semisolid transparent products that are stabilized through appropriate gelatinizing agents. A distinction is made between oleogels (anhydrous), hydrogels (oil free) and oil/water gels. The choice of type will depend on the desired intended application. The oil/water gels have high emulsifier contents and have certain advantages in comparison with emulsions from the standpoint of both aesthetics and applications.

Other cosmetic agents include agents for influencing body odor. Deodorizing agents are intended here, in particular. Such deodorants may mask, remove or destroy odors.

Unpleasant body odors are formed from bacterial decomposition of perspiration, in particular, in the moist, warm axillary cavities, where microorganisms find good conditions for survival. Accordingly, the most important ingredients of deodorants are microbistatic substances. In particular, such microbistatic substances that have a largely selective efficacy with respect to the bacteria responsible for body odor are possible. Non-limitingactive ingredients, however, have only a bacteriostatic effect and by no means completely kill off the bacterial flora. The microbistatic agents may in general include all suitable preservatives with a specific action against gram-positive bacteria. For example, these include Irgasan DP 300 (trichlosan, 2,4,4'-trichloro-2'-hydroxydiphenyl ether), chlorhexidine (1,1'-hexamethylenebis(5-(4'-chlorophenyl)biguanide) as well as 3,4,4'-trichlorocarbanilide. Quaternary ammonium compounds are also suitable in principle. Because of their high antimicrobial efficacy, all these substances are used only in low concentrations of 0.1 to 0.3 wt.-%. In addition, numerous perfumes also have antimicrobial properties. Accordingly, such perfumes having antimicrobial properties are used in deodorants. Farnesol and phenoxyethanol may be mentioned here. It is therefore possible, if the inventive deodorants contain such perfumes which have their own bacteriostatic effect. Another group of important ingredients of deodorants is the enzyme inhibitors, which inhibit the decomposition of perspiration through enzymes such as citric acid triethyl ester or zinc glycinate. Essential ingredients of deodorants also include the antioxidants, which should prevent oxidation of the components of perspiration.

The inventive compounds and agents under ambient conditions have a good hydrolytic cleavability. They also have good stability in storage in an alkaline environment, such as that encountered in detergents and dishwashing agents, for example.

In a non-limiting embodiment, at least one compound of formula (I) or the mixture of compounds of formulae (I) and (II) release scent aldehyde as scent. In a further embodiment these compounds are used with further scents, different from compounds of formulas (I) and (II).

The present embodiments further pertain to detergent, cleaning, fabric softener or cosmetic composition comprising at least one compound according to embodiment 1 or a mixture according to embodiment 2. In a non-limiting embodiment the at least one compound according to embodiment 1 or the mixture according to embodiment 2 is present in 0.000001 to 5 wt.-%, such as 0.00001 to 2 wt.-%, alternatively 0.0001 to 1 wt.-%, or in 0.0001 to 0.1 wt.-%, based on the total weight of the composition. In another embodiment the composition is solid, liquid or a gel or in the form of a dosage unit comprising a mixture thereof. Furthermore, it is possible that the detergent or cleaning composition is a powder, granule, tablet or tab or wherein the liquid is a solution, emulsion or dispersion or a form where solid and liquid, or solid and gel or liquid and gel parts are present in one dosage unit, for example in a pouch, the cleaning composition is liquid or gel and suitable for hard surfaces, such sa it is a multi purpose cleaner, or comprising an alkaline or acidic composition, a glass cleaner, such as having anti-rain properties, or a floor or bathroom cleaner.

In an alternative embodiment the cosmetic composition is an aqueous cosmetic composition comprising surfactants and is in particular suitable for cosmetically, non-therapeutic, treating keratin fibers or skin. In a non-limiting embodiment, this cosmetic composition changes the body odor of a being, in particular it is a deodorant composition.

Moreover, a method for prolonging the scent of detergent, cleaning, fabric softener or cosmetic compositions or of surfaces which have been treated with these compositions is also disclosed, in particular for hard or textile surfaces, wherein the detergent, cleaning, fabric softener or cosmetic composition is used. In a non-limiting embodiment the composition is a detergent composition and/or the surface which has been treated with is a textile, such as selected from blended fabric, cotton, or polyester.

EXAMPLES

Synthesis of 1-aza-3,7-d ioxabicyclo[3.3.0]octanes

AA1: General operating procedure for synthesis of 1-aza-3,7-dioxabicyclo[3.3.0]octanes, amino alcohol/aldehyde ratio 1:2.

The amino alcohol and the aldehyde were combined in a 1:2 molar ratio in toluene as the solvent under nitrogen atmosphere. The reaction mixture was heated to 120° C., whereupon the amino alcohol slowly goes into solution. The mixture was refluxed using a water separator for 7 hours. The resulting product was obtained by removing the solvent by rotating vacuum distillation and drying in high vacuum.

AA2: General operating procedure for synthesis of 1-aza-3,7-dioxabicyclo[3.3.0]octanes, amino alcohol/aldehyde ratio 1:2 in situ.

The amino alcohol was combined with the aldehyde in a 1:2 molar ratio under nitrogen atmosphere. The reaction mixture was heated to 100-140° C., whereupon the reactants go into solution slowly or melt. The reaction mixture is heated until no more reaction water can be distilled off. The transparent slightly yellowish solution was dried in a high vacuum.

Example 1: Synthesis of 2,8-bis(2-phenylpropyl)-5-methyl-3.7-dioxa-1-azabicyclo[3.3.0]octane 3-Phenylbutanal (CAS 16251-77-7) was combined with 2-Amino-2-methyl-1,3-propandiol (CAS 115-69-5) in a 2:1 molar ratio under nitrogen atmosphere. The mixture was heated to 100° C.-110° C., reaction water is removed using a water separator. The reaction mixture is heated until no more reaction water can be distilled off, supported by vacuum if necessary. A light yellow product is obtained (yield 93%).

Comparative Example 1

Instead of 3-methyl-3-phenylpropanal the aldehyde llial was used. The synthesis was carried out as described for the inventive example above.

Olfactory Test

The aldehydes trifernal and llial in free form as well as the compound of Example 1 and Comparative Example 1 were tested for their performance as follows. The afore-mentioned compounds were mixed into a standard solid powder detergent (65 g dose (Persil)) so that the initial scent intensity of the free compounds trifernal and filial on the one hand and the scent intensity of the respective oxazolidine precursors was about the same. The scent intensity was evaluated by four trained perfumers on a scale of 0 to 5, where 5 is the highest score and 0 stands for no perception of scent. The scent was evaluated on textiles after washing 3.5 kg laundry in a standard washing machine (standard program at 40° C.). Three different types of laundry were used, namely blended fabric, cotton and polyester. The scent was evaluated on the laundry being in wet state directly after washing, in dry state immediately after the laundry had dried and 7 days after the washing/drying. The assessment was performed 5 times, respectively and the results are displayed as average values. The results are displayed in Table 1 below.

Definition of the Scale
5 very strong
4 strong
3 pleasant
2 perceptible
1 not perceptible

TABLE 1

Results of the olfactory test.

| Compound | Wet (1) | Wet (2) | Wet (3) | Dry (1) | Dry (2) | Dry (3) | After 7 days (1) | After 7 days (2) | After 7 days (3) |
|---|---|---|---|---|---|---|---|---|---|
| Example 1 | 5.00 | 5.00 | 4.00 | 4.00 | 5.00 | 3.00 | 4.67 | 5.0 | 3.67 |
| Trifernal | 1.50 | 1.50 | 1.50 | 1.00 | 1.00 | 1.00 | 3.0 | 2.67 | 2.83 |
| Comparative Example 1 | 2.13 | 2.38 | 2.38 | 2.00 | 2.50 | 2.50 | 2.75 | 3.25 | 3.00 |
| Lilial | 2.13 | 2.50 | 2.25 | 2.00 | 2.75 | 2.25 | 2.75 | 3.00 | 3.00 |

(1) = blended fabric, (2) = cotton, (3) = polyester
Scent impression of the dosing units before washing Trifernal = 5.0;
Example 1 = 2.00;
Lilial = 3.4;
Comparative Example 1 = 2.2.

As can be seen by the results shown in Table 1, the compounds of example 1 show an improved long-lasting scent impression compared to the compounds of comparative example 1.

The invention claimed is:

1. A composition comprising a compound based on 1-Aza-3,7-dioxabicyclo[3.3.0]octane substituted with 2-phenylpropyl represented by formula (I)

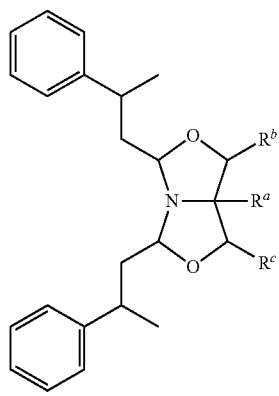

(I)

wherein $R^a$ is hydrogen or a $C_{1-20}$ alkyl;

the $C_{1-20}$ alkyl is optionally substituted with hydroxyl groups or amine groups; up to 8 —$CH_2$— groups of the $C_{1-20}$ alkyl are substituted by —O— groups; and the up to 8 —$CH_2$— groups are not adjacent to each other; and $R^b$ and $R^c$ are independently selected from hydrogen or $C_{1-6}$ alkyl;

wherein the composition is a detergent, fabric softener, cosmetic composition, or combinations thereof.

2. The composition of claim 1, further comprising at least one compound of formula (II)

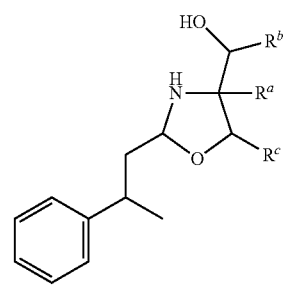

(II)

wherein $R^a$ is hydrogen or a $C_{1-20}$ alkyl;

the $C_{1-20}$ alkyl is optionally substituted with hydroxyl groups or amine groups; up to 8 —$CH_2$— groups of the $C_{1-20}$ alkyl are substituted by —O— groups; and the up to 8 —$CH_2$— groups are not adjacent to each other; and $R^b$ and $R^c$ are independently selected from hydrogen or $C_{1-6}$ alkyl;

wherein the composition is a detergent, fabric softener, cosmetic composition, or combinations thereof.

3. The composition of claim 1, wherein the at least one compound represented by formula I is present in an amount ranging from 0.000001 to 5 wt. %.

4. The composition of claim 1, wherein the composition is in the form of a solid, a liquid, a gel dosage unit, and combinations thereof.

5. The composition according to claim 4, wherein the solid is a powder, granule, tablet, or tab, wherein the liquid is a solution, emulsion, or dispersion, or wherein a dosage form where solid and liquid or solid and gel or liquid and gel parts are present in one dosage unit.

6. The composition of claim 1, wherein the composition is an aqueous cosmetic composition comprising one or more surfactants.

7. The composition of claim 1, wherein the composition is a deodorant composition.

8. The composition of claim 1, wherein the compound represented by formula I releases the fragrance compound of formula (IV):

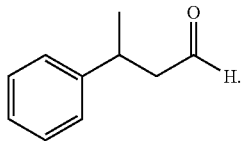
(IV)

9. The composition of claim 1, further comprising one or more additional fragrance compounds different from that of the compound of formula (I).

10. The composition of claim 1, wherein $R^a$ of the compound of formula (I) is a $C_{1-6}$ alkyl.

11. The composition of claim 1, wherein $R^a$ of the compound of formula (I) is methyl.

12. The composition of claim 1, wherein $R^a$ of the compound of formula (I) is hydrogen.

13. The composition of claim 1, wherein $R^b$ and $R^c$ of the compound of formula (I) are independently selected from hydrogen or methyl.

14. The composition of claim 1, wherein $R^b$ and $R^c$ of the compound of formula (I) are both hydrogen.

15. The composition of claim 2, wherein $R^a$ of the compound of formula (II) is a $C_{1-6}$ alkyl.

16. The composition of claim 2, wherein $R^a$ of the compound of formula (II) is methyl.

17. The composition of claim 2, wherein $R^a$ of the compound of formula (II) is hydrogen.

18. The composition of claim 2, wherein $R^b$ and $R^c$ of the compound of formula (II) are independently selected from hydrogen or methyl.

19. The composition of claim 2, wherein $R^b$ and $R^c$ of the compound of formula (II) are both hydrogen.

* * * * *